United States Patent
Maurer et al.

(10) Patent No.: US 8,962,708 B2
(45) Date of Patent: Feb. 24, 2015

(54) POLYETHER GROUP CONTAINING DENTAL COMPOSITION CONTAINING AN F-CONTAINING COMPOUND, PROCESS OF PRODUCTION AND USE THEREOF

(75) Inventors: Andreas R. Maurer, Langenneufnach (DE); Christoph Schulte, Windach (DE); Peter U. Osswald, Tuerkheim (DE); Joachim W. Zech, Kaufering (DE); Hendrik Grupp, Inning a Ammersee / Bacherna Woerthsee (DE); Peter Bissinger, Diessen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 84 days.

(21) Appl. No.: 13/322,970

(22) PCT Filed: Jun. 9, 2010

(86) PCT No.: PCT/US2010/037906
§ 371 (c)(1),
(2), (4) Date: Nov. 29, 2011

(87) PCT Pub. No.: WO2010/147817
PCT Pub. Date: Dec. 23, 2010

(65) Prior Publication Data
US 2012/0077900 A1 Mar. 29, 2012

(30) Foreign Application Priority Data
Jun. 15, 2009 (EP) ................................. 09162681

(51) Int. Cl.
*A61K 6/10* (2006.01)
*A61K 6/08* (2006.01)
*A61K 6/087* (2006.01)
*C08L 71/02* (2006.01)
*C08L 83/12* (2006.01)
*A61K 6/083* (2006.01)

(52) U.S. Cl.
CPC . *A61K 6/10* (2013.01); *A61K 6/083* (2013.01); *A61K 6/087* (2013.01)
USPC ......... 523/109; 523/115; 433/214; 433/228.1

(58) Field of Classification Search
CPC ........... A61K 6/10; A61K 6/08; A61K 6/087; C08L 71/02
USPC .................. 523/109; 433/214; 524/368, 861; 528/20
See application file for complete search history.

(56) References Cited

U.S. PATENT DOCUMENTS

| | | | |
|---|---|---|---|
| 4,657,959 A | 4/1987 | Bryan et al. | |
| 6,861,457 B2 * | 3/2005 | Kamohara | 523/109 |
| 7,754,795 B2 * | 7/2010 | Hintzer et al. | 524/284 |
| 7,790,781 B2 * | 9/2010 | Bublewitz et al. | 523/109 |
| 7,812,065 B2 * | 10/2010 | Bublewitz et al. | 523/109 |
| 8,007,579 B2 * | 8/2011 | Klettke et al. | 106/38.2 |
| 8,466,210 B2 * | 6/2013 | Zech et al. | 523/109 |
| 2008/0319100 A1 * | 12/2008 | Bublewitz et al. | 523/109 |

FOREIGN PATENT DOCUMENTS

| | | |
|---|---|---|
| DE | 10 2006 001126 | 7/2007 |
| EP | 2 072 029 | 6/2009 |
| GB | 2 337 524 | 11/1999 |
| WO | WO 2007/080071 | 7/2007 |
| WO | WO2009/079534 | * 6/2009 |

OTHER PUBLICATIONS

PCT International Search Report for PCT Application No. PCT/US2010/037906 dated Jul. 28, 2010, 3 pages.

* cited by examiner

*Primary Examiner* — Tae H Yoon
(74) *Attorney, Agent, or Firm* — 3M Innovative Properties Company; Qiang Han

(57) ABSTRACT

The invention relates to a curable dental composition comprising a curable polyether group containing polymer as component (A), an initiator capable of initiating a curing reaction of component (A) as component (B) and a certain F-containing compound as component (C). The invention also relates to a method of production and use of the curable dental composition or a respective kit of parts for the preparation of or as impression material or for the preparation of crowns and bridges.

23 Claims, No Drawings

POLYETHER GROUP CONTAINING DENTAL COMPOSITION CONTAINING AN F-CONTAINING COMPOUND, PROCESS OF PRODUCTION AND USE THEREOF

CROSS REFERENCE TO RELATED APPLICATIONS

This application is a national stage filing under 35 U.S.C. 371 of PCT/US2010/037906, filed Jun. 9, 2010, which claims priority to European Application No. 09162681.2, filed Jun. 15, 2009, the disclosure of which is incorporated by reference in its/their entirety herein.

The invention relates to a curable dental composition comprising a polyether group containing polymer and an F-containing compound. The dental composition can be used e.g. as dental impression material and/or for the production of crown and bridges.

BACKGROUND ART

Dental impression materials are well known in the art and have been applied for a long time. Such materials typically possess a variety of properties including a quick setting behavior, good dimensional stability and sufficient storage stability. Generally, the materials are provided in two components to be mixed prior to use and cure by a crosslinking-reaction.

One widely used class of impression materials is based on addition- or condensation crosslinking-reactions of polyorganosiloxane containing components.

Dental impression materials containing polyorganosiloxane components are typically hydrophobic in nature. In order to make these materials more hydrophilic, the incorporation of surfactants has been proposed. Measuring the contact angle of a water drop on the surface of the mixed composition is an appropriate method to find out to which extent the composition has a hydrophilic or hydrophobic behavior.

U.S. Pat. No. 4,657,959 relates to hydrophilic silicones and contains examples of compositions containing amphoteric and ionic surfactants. With regard to non-ionic fluor-containing surfactants, perfluorinated groups are attached to a polyether moiety via a polyvalent hydrocarbonyl linking group (e.g. —$C_2H_4$— or —$SO_2NR$— group).

GB 2,337,524 mentions a silicone composition for oral mucosa impression. The composition i.a. comprises an organopolysiloxane having at least two aliphatic unsaturated hydrocarbons in one molecule and a certain amount of one or two or more non-ionic surfactants.

WO 2007/080071 A2 describes addition-cured dental impression materials based mainly on silicones which provided hydrophilicity in the non-cured pasty state. By application of mixtures of fluorinated surfactants and silicone surfactants water contact angles of the pasty material below 10° were obtained 40 s (seconds) after mixing of the base and catalyst paste and 3 s after setting of the drop on the surface. The non-ionic fluorinated surfactants described contain at least one partly or per-fluorinated hydrocarbon rest, which is connected via an oxygen atom, an amino or a keto group, carboxylic ester group, a phosphoric acid ester and/or amide with an (poly)alkylenoxide radical, an carbohydrate radical, an aliphatic polyhydroxy radical or a nitrogen-containing heterocyclic compound or is at least a per- or partly fluorinated rest which comprise at least one amino-oxide rest.

The fluorinated surfactants taught in WO 2007/080071 A2, however, may not be very suitable for use in dental applications. It was found that generally the surfactants disclosed in this reference may have an adverse impact on other desirable properties of the dental composition. E.g. the fluorinated surfactants described in this reference may cause difficulties during the production process of the dental impression material, e.g. during a de-gassing step needed for producing high quality and gas free compositions.

DESCRIPTION OF THE INVENTION

It would now be desirable to provide curable compositions for making dental impressions that can be manufactured and provided in an easy and convenient way.

It may also be desirable to find a curable composition which has a reduced tendency to produce foams during a de-gassing step or which can be de-gassed more efficiently.

Ideally, the curable composition cures within a reasonable period of time and provides enough working time before curing to be useful as a dental impression material.

In one aspect, the invention provides a curable dental composition comprising
 a curable polyether group containing polymer as component (A),
 an initiator capable of initiating a curing reaction of component (A) as component (B),
 an F-containing compound as component (C), wherein the F-containing compound has the following formula:

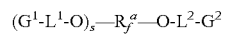

$(G^1-L^1-O)_s—R_f^a—O-L^2-G^2$ wherein:
 $G^1$ and $G^2$ each independently represents a non-ionic endgroup that is free of polyoxyalkylene groups or contains polyoxyalkylene such that the total amount thereof in the F-containing compound is not more than 10% by weight based on the molecular weight of the F-containing compound;
 $L^1$ and $L^2$ each independently represents an aliphatic hydrocarbon group or a partially or fully fluorinated aliphatic hydrocarbon group;
 $R_f^a$ represents a mono-valent or divalent partially or fully fluorinated aliphatic group or a partially or fully fluorinated aliphatic group interrupted by one or more oxygen atoms;
 with the proviso that at least one of the following conditions is fulfilled:
  (i) at least one of the moieties $L^1$-$G^1$ and $L^2$-$G^2$ is partially or fully fluorinated or
  (ii) $R_f$ is a partially or fully fluorinated aliphatic group interrupted by one or more oxygen atoms.

By the term "non-ionic end group" is meant an end group that is free of groups that dissociate into ionic species in an aqueous medium. Examples of ionic groups include acid groups as well as salts.

In a particular embodiment $G^1$ and $G^2$ are independently selected from: —$COOR^a$, —$CONR^bR^c$, —$CH_2OH$, —$CF_2OR^a$, —$CHFOH$, —$CHFOR^a$, —$CH_2OR^a$ or —F with $R^a$ representing an aromatic or aliphatic hydrocarbon group optionally being substituted with a hydroxy or amino group or a halogen atom and $R^b$ and $R^c$ independently representing H or an aromatic or aliphatic hydrocarbon group optionally being substituted with a hydroxy or amino group or a halogen atom.

Further in a particular embodiment, $G^1$ and/or $G^2$ may include a group that is capable of participating in the cross-linking reaction between components (A) and (B). Accordingly, in one embodiment, either or both end groups may be substituted with a functional group capable of reacting with either component (A) or (B).

In a further particular embodiment, the invention relates to a dental composition comprising

- a curable polyether group containing polymer as component (A),
- an initiator capable of initiating a curing reaction of component (B) as component (B),
- at least one F-containing compound as component (C), wherein the F-containing compound has the following formula

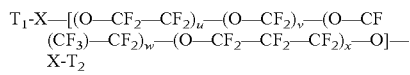

with u=0 to 8, v=0 to 8, w=0 to 8 and x=0 to 8 and u+v+w+x≥1, wherein $T_1$ and $T_2$ can be equal or different and are independently selected from —COOR, —CONR$^b$R$^c$—CH$_2$OH, —CF$_2$OR, —CHFOH, —CHFOR, —CH$_2$OR or —F with R and being a linear or branched alkyl chain (C1 to C9), aryl chain (C1 to C9) or alkylaryl chain (C1 to C9) each of which may optionally be substituted with one or more substituents selected from the group consisting of hydroxyl, amino group, halogen atom, a SiH group or a group capable of reacting with SiH, R$^b$ and R$^c$ independently representing H or having a meaning as given for R and wherein X is selected from —(CF$_2$)$_{1-6}$—, —CF(CF$_3$)— and —CHF—CF$_2$—.

optionally an Si-containing surfactant as component (D1), and optionally an hydrocarbon surfactant as component (D2).

An example of a group capable of reacting with SiH and that may be included in either or both of the end groups $T_1$ and $T_2$ includes a vinylsiloxane group such as for example a vinyldialkyl siloxane including for example CH$_2$=CH—Si(CH$_3$)—.

According to another aspect, the invention features a kit of parts comprising a base paste and a catalyst paste separated from each other before use, wherein the base paste comprises component (A) and the catalyst paste comprises component (B) and wherein component (C), (D1), (D2), and other (optional) components can be present either in the base paste or the catalyst paste or the base paste and the catalyst paste, wherein components (A) to (D2) are as described in the text of the invention.

A further aspect of the invention is directed to a method of producing a dental composition comprising the step of combining an F-containing compound with a polyether group containing polymer, wherein the F-containing compound is as described the text of the invention.

In yet another embodiment, the invention relates to a method of using the inventive dental composition as impression materials or for the preparation of crowns and bridges.

It has been found that the addition of an F-containing compound as described in the text of the invention to a composition comprising a curable polyether group containing polymer has an impact on the degassing behavior of the composition, especially during the manufacturing process.

Dental impression materials typically contain curable polymers or pre-polymers having a certain viscosity which have to be mixed with the other components present in the composition, like fillers. Due to the viscous components present in the mixture, the mixing process often involves a kneading step. During such a kneading step, air is often introduced or dissolved in the mixture and has to be removed later. Otherwise, the resulting mixture will contain air or gas residues which may cause defects in the process of making impressions of dental tooth structure later. E.g., the cured dental impression may contain undesired air bubbles and thus may lead to an imprecise impression, if the air is not removed previously.

Thus, during the manufacturing process, the mixture has to be de-gassed, e.g. by applying reduced pressure, while continuing the mixing or kneading step.

Such a de-gassing step or process is typically time and money consuming. Thus, it is desirable to either reduce the time needed for applying reduced pressure or to speed up the process by reducing or lowering the pressure applied to the mixture.

Surprisingly, it has been found that the F-containing compound of the invention is suitable to address this problem. The inventive compositions can more easily be de-gassed during the production process.

This is in contrast to compositions containing other fluorinated surfactants, such as the ethoxylated nonionic fluorosurfactant Zonyl™ FSO-100 (DuPont), which is also described in WO 2007/080071 A2.

Furthermore, the F-containing compound typically has no or a limited solubility in water and thus has no tendency to migrate out of the impression material into the tissue of the patient to be treated.

It has been found that generally the F-containing compounds used according to the invention, despite their limited solubility characteristics in water, nevertheless are generally capable of improving the hydrophilicity of the curable composition, initially and/or in the cured state. Thus, the wetting behavior of the composition with respect to hydrophilic surfaces (including human skin, mucosa, gingiva and dental tooth structure) is typically improved.

Moreover, the F-containing compounds have typically no or little adverse affects on other desired properties of the curable composition and may even improve some desired properties.

Furthermore, with respect to some embodiments, it has also been revealed that a cured dental composition containing the F-containing compound as described in the text of the invention in combination with a surfactant typically shows improved storage stability, e.g. compared with a dental composition containing the F-containing compound suggested in the examples of WO 2007/080071 A2.

With respect to certain embodiments of the invention, it has been found that the setting characteristics are improved in that the composition typically cures more rapidly, however, without negatively affecting the working time.

DEFINITIONS

Within the description of the invention, the following terms are defined as follows:

The term "compound" is a chemical substance which has a particular molecular identity or is made of a mixture of such substances, e.g., polymeric substances.

The term "hydrosilation" means the addition of an organopolysiloxane compound comprising SiH-group(s) to a compound containing an aliphatic multiple bond (e.g., an olefinic or acetylenic unsaturation), preferably a vinyl group, i.e. —CH=CH$_2$.

By "paste" is meant a soft, viscous mass of solids dispersed in a liquid.

The term "silicone" refers to a polymer having, for the most part, alternating silicon and oxygen atoms (i.e., a polysiloxane chemical structure). If the silicone has sufficient pendant functional groups, the silicone may undergo a setting reaction in the presence of a crosslinker compound and a catalyst compound.

A "hardenable matrix" may be described as the components of a composition contributing to the formation of a network due to chemical interaction (e.g. formation of chemical bondings) between the components thereby leading to a significant change in rheological properties like viscosity.

The terms "vulcanizing", "hardening", "crosslinking" and "setting" are used interchangeable and refer to compositions that have as a common attribute the development of a crosslinked elastomer from relatively low molecular weight linear or branched polymers or pre-polymers by means of a chemical reaction that simultaneously forms these crosslinks and effectively extends chain length at room temperature.

"Room temperature vulcanizing" implies that the curing reaction can proceed at temperatures at or near about 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

The term "crosslinked polymer" as used herein, refers to polymers that react with the functional group or groups of the polymer chains to lengthen them and connect them, e.g., to form a crosslinked network. In contrast to a thermoplastic polymer (i.e., a polymer that softens and flows upon heating) a crosslinked polymer, after crosslinking, is characteristically incapable of further flow.

The term "working time" as used herein, refers to the time between the initiation of the setting reaction (e.g., when a polyether group containing polymer bearing reactive groups and an initiator, being able to start the curing reaction of the polymer are mixed) and the time the setting reaction has proceeded to the point at which it is no longer practical to perform further physical work upon the system, e.g., reform it, for its intended purpose. When the reaction has proceeded to this later point the material is said to have reached its "gel point". The working time preferably provides enough time to mix and place the composition into its desired form. For many dental impression compositions and applications the working time under conditions of use can be greater than about 30 s (seconds), or greater than about 1 min (minute), or greater than about 2 min. Thus, the working time is typically within a range of about 30 s to about 3 min or about 1 min to about 2 min. So-called "fast-setting" compositions typically have a shorter working time, e.g. less than about 2 min or less than about 1.5 min.

The terms "set time" or "setting time" as used herein, refer to the time at which sufficient curing has occurred so that essentially the material's final cured-state properties are obtained. For a polyether group containing impression material the set time is that time at which one may remove the material from the surface being replicated without causing permanent deformation of the material. The setting time may be approximated, e.g., by measuring the torque of the reacting composition on an oscillatory rheometer. When the torque value reaches a maximum value the material is said to be fully set. An arbitrary torque value which is less than the typical maximum value (e.g. 90% of the maximum value) may alternatively be used as a practical approximation of the set time. In general, shorter setting times are preferred over longer setting times. For dental impression compositions the setting time occurs at a time preferably less than about 10 min after initiation of the reaction. More preferably the setting time is less than the sum of about 5 minutes plus the working time. Most preferably the setting time is just longer than the desired working time.

More specifically, the setting time is the time between positioning of the spoon with the dental material in the mouth of the patient and removal of the cured material, and can also be called the mouth residence time or period. Setting times of <about 3 min mouth residence time, preferably <about 2.5 min, and particularly preferably <about 2 min are desirable properties for the dentist working with situation impression materials. For example, the one-phase impression material Imprint™ (3M ESPE) has a setting time of about 5 minutes, while a typical alginate impression material such as Palgat™ (3M ESPE) has a setting time of about 4 min.

By "dental composition" is meant a composition which is intended and adapted to be used in the dental field (including restorative and prosthodontic work) including the orthodontic area. In this respect, a dental composition typically does not contain hazardous substances. Commercially available products have to fulfil requirements such as those given in ISO 4823. Typically, those compositions cure or set at ambient conditions.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is carried out by placing a liquid material into the mouth in a customised tray. The material then sets to become an elastic solid, and when removed from the mouth retains the shape of the teeth. Common materials used for dental impressions are sodium alginate, agar, polyethers including aziridino substituted polyether materials and silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

A "prepolymer" is defined as a compound or a mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture with increased molecular weight compared to the prepolymer.

"Polyether" or "polyether group containing compound" are compounds having a molecular weight of at least about 150 g/mol and containing in the backbone at least about 3, 10 or 20 ether moieties. Polyethers can also be defined as polyalkylene oxides or compounds comprising polyalkylene oxide moieties. Polyether containing compositions used as dental impression material can be cured by different mechanisms. Widely used is curing caused by the reaction of aziridino groups with each other. A suitable definition for polyether can further be found e.g. in Römpp Lexikon Chemie—Vers. 2.0, 1999; Georg Thieme Verlag 1999. Polyethers are polymers having repeating units which are joined together by ether moieties (C—O—C). This is in contrast to polymers with side groups containing ether moities, side groups attached to the backbone of the polymer.

"Surfactants", also sometimes referred to as tensides, are wetting agents that are able to lower the surface tension of a liquid, allowing easier spreading, and lower the interfacial tension between two liquids.

Surfactants are usually organic compounds that are amphiphilic, meaning they contain both hydrophobic groups ("tails") and hydrophilic groups ("heads"). Typical examples include polyethyleneglycol-substituted fatty acids.

Usually, a surfactant can be classified by the presence of formally charged groups in its head. A nonionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitterionic.

Surfactants typically reduce the surface tension of water by adsorbing at the liquid-gas interface. They also may reduce the interfacial tension between oil and water by adsorbing at the liquid-liquid interface. Many surfactants can also assemble in the bulk solution into aggregates. Some of these aggregates are known as micelles. The concentration at which surfactants begin to form micelles is known as the critical micelle concentration (CMC).

Surfactants can also be characterized by a "Hydrophobic Lipophilic Balance" value (HLB-value). Generally, with an increasing HLB-value a substance becomes more hydrophobic and in reverse more lipophilic. The measurement of the HLB-value of a certain substance can be accomplished by determining its aqueous solubility and cloud point, using e.g. the method described by H. Schott, J. Pharm. Science, 58, 1442, (1969). E.g. according to the product description, Silwett L-77 (a Si-containing surfactant) is said to have an estimated HLB value in the range of 5 to 8.

The "initial water contact angle" is defined as the contact angle of a water drop at the time 0 seconds (s) of the experiment ($\theta_{0s}$ in degrees). The starting time of the experiment is defined as the time when the cannula, which is used for setting the water drop on a surface, does not have an influence on the shape of the water drop, i.e. when the cannula was removed from the water drop as soon as possible after placing of the water drop. Thus, ideally this time corresponds to the first contact of the water drop to the surface. Furthermore, the initial contact angle can be determined for any time after mixing of base paste and catalyst paste. The term "initial" does not refer to the time after mixing. The initial contact angle can be determined from Water Contact Angle Measurement as described in more detail in the Example section below, using e.g. a goniometer DSA 10 (Krüss). A low water contact angle typically indicates a better wettability.

The term "automixer-suitable impression material" relates to a multi-component impression material which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™", "Pentamix™2" and "Pentamix™3" devices of 3M ESPE Company (cf. U.S. Pat. No. 5,286,105 and U.S. Pat. No. 5,249,862).

By a "temporary or long term crown and bridge material" is meant a material, which is used for the preparation of dental crowns and bridges containing hardenable monomers, including (meth)acrylates. These materials are typically used during the time period needed for making a permanent restoration. A typical time period ranges from a few days (e.g. 3 to 5) over weeks (1 to 3) to a few months (1 to 6). A long term crown and bridge material is typically used over a time period of about 6 to about 24 month.

The term "molecular weight" refers to the number average of the molecular weight, as is conventionally determined for the individual classes of polymers by gel permeation chromatography (GPC) against a standard of defined molecular weight. Suitable measurement methods will be known to the person skilled in the art.

Furthermore, the determination of the molecular weights and the molecular weight distribution of polymeric polyols can be carried out, for example, by means of end group determination, for example by nuclear magnetic resonance (NMR) methods. Also suitable for the determination of the molecular weights and the molecular weight distribution of polymeric polyols is the determination of the hydroxyl value.

If desired, a suitable method of determining the molecular weight (Mw and Mn) and molecular weight distribution of organic diols can be carried out by means of GPC using a column combination PSS SDV 10,000 Å+PSS SDV 500 Å+PSS SDV 100 Å with column dimensions of 8×300 mm and a particle size of 5 µm. As a pre-column there is used a PSS SDV 100 Å having column dimensions of 8×50 mm and a particle size of 10 µm. THF stabilised with 200 ppm of Ionol, at a flow rate of 1.0 ml/min, is especially suitable as the mobile phase. As the detector there is used a refractive index (RI) detector; the injection volume for the samples (1% w/w weighed into the mobile phase) is 100 µl. As the standard solution there is used a polystyrene standard series (0.1% w/w weighed into the mobile phase). The evaluation is carried out according to the principle of relative GPC using an automatic evaluation module (TurboSEC Software) by means of comparison of the volumes of sample eluted with the volumes of the polystyrene standard series eluted. Mn, Mw and polydispersity are evaluated.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

Certain embodiments of the curable dental composition can be characterized by at least one or more of the following features:
  Consistency (according to ISO 4823): 0, 1, 2 or 3 and/or
  Setting time: within about 15 min after mixing at ambient conditions (e.g. 23° C.).

That is, the curable dental composition (that is, in its uncured state) can show a comparable low viscous behaviour (consistency 3), a medium viscosity (consistency 1 or 2) or show a putty-like behaviour (consistency 0).

Certain embodiments of the cured dental composition can be characterized by at least one or more of the following features:

Tensile strength (according to DIN 53504): at least about 0.2 MPa, or at least about 1.0, Elongation at break (according to DIN 53504): at least about 30%, or at least about 50%, or at least about 100%, Recovery from deformation (according to ISO 4823): at least about 90%, or at least about 95%, or at least about 98%, Shore A hardness (according to DIN 53505; 24 h): at least about 20 or at least about 30.

If desired, the water contact angle can be measured as follows:

For the preparation of test piece the mixed paste is subjected to an object slide and flattened and triturated by a second object slide in order to obtain a thin film. The test piece preparation is performed in that simplified way as the thickness of the film does not have a significant effect on the measured water contact angle (see G. Kugel, T. Klettke, J. A. Goldberg, J. Benchimol, R. D. Perry, S. Sharma, *J Prosthod.* 2007, 16, 84-92). The object slide is placed on the table of a prop Shape Analyse System DSA 10 (Krüss GmbH, Hamburg), a well known device for measuring contact angles. 5 µl of water are placed onto the surface of the specimen and an automatic contact angle measurement is started using standard software of the goniometer. Measuring time is at least about 10 s up to about 200 s. The water contact angle is measured at different time periods after mixing of base paste and catalyst paste, especially after 40 and 60 s. The data (video sequences) is evaluated by the "circle fitting" method, another standard method for data evaluation (see G. Kugel, T. Klettke, J. A. Goldberg, J. Benchimol, R. D. Perry, S. Sharma, *J. Prosthod.* 2007, 16, 84-92). $\Theta_{10s}$ is the angle obtained 10 s after placing the water drop on the surface. $\Theta_{0s}$ is the angle obtained immediately after placing the water drop on the surface (initial water contact angle).

If desired, the viscosity can be measured at 23° C. using a Physica/Anton Paar (MCR 300 or MCR 301) device with a plate/plate system (diameter 20 mm) and a slit of 0.2 mm. The viscosity values (Pas) and share stress values (Pa) are recorded for each share rate (γ starting from 10 1/s to 100 1/s in 10 1/s and/or 5 1/s steps. For each share rate, a delay of 5 s is used before collecting data. The above mentioned method of measurement corresponds essentially to DIN 53018-1.

If desired, the setting time of the compositions can be determined by measuring the viscosity of the mixed base and catalyst paste in dependence on the time at 23° C. and 50% humidity by using a Physica/Anton Paar (MCR 300 or MCR 301) rheometer (plate/plate measurement system) from Anton Paar. The setting time "te" as well as the working time "ta" are typically determined with the software supplied with the instrument.

If desired, the tensile strength and elongation of the compositions can be determined according to DIN 53504. The tensile strength is given in MPa and the elongation in % of the original length. Tensile strength and elongation data are evaluated by tearing six 1-shaped specimens with a central unit of 20 mm×4 mm×2 mm in a Zwick Z020 Universal testing machine. Base and catalyst pastes can be mixed through a static mixer (SulzerMixpac Comp.) or by hand and filled into a brass mould. After 24 h at about 23° C. the specimen are removed, six measurements are made and the mean value determined (speed 200 mm/min).

The dental composition according to the invention includes a polyether group containing polymer as component (A), an initiator capable of initiating a curing reaction of component (A) as component (B), an F-containing compound as component (C) and optionally two surfactants (D1 and D2) differing from each other with respect to their chemical structure.

The inventive dental composition includes a polyether group containing polymer as component (A), that is, a polymer comprising a polyether group and reactive moieties which upon addition of a suitable catalyst or initiator can react with each other and thus forming a polymeric network.

According to the invention, the curable dental compositions can generally comprise any multiplicity of types of compounds which, when mixed shortly before taking an impression, result in the formation of a rubber like impression material due to a polymerization reaction. Generally, polyaddition, ring-opening polymerization (including the ring-opening of aziridines), metathesis and polycondensation are preferred types of polymerization reactions, wherein polyaddition and ring-opening polymerization are sometimes preferred.

Component (A) is typically present in an amount, which allows the formation of a sufficiently crosslinked network, in order to fulfil the practitioners needs.

Component (A) is typically present in an amount of at least about 5 wt.-% or at least about 12 wt.-% or at least about 20 wt.-%, wt.-% with respect to the whole composition.

Component (A) is typically present up to an amount of about 97 wt.-% or up to about 90 wt.-% or up to about 85 wt.-% wt.-% with respect to the whole composition.

Typical ranges include from about 5 wt.-% to about 97 wt.-% or from about 12 wt.-% to about 90 wt.-% from about 45 wt.-% to about 60 wt.-%.

The molecular weight (Mn) of the polyether group containing polymer is typically in a range from about 150 to about 20,000 g/mol, or in the range from about 250 to about 10,000 g/mol, determined e.g. with GPC methods know to the person skilled in the art.

Suitable polyethers or polyether groups, which can be used, include those which meet the requirements in terms of material properties with regard to the preferred use as dental materials.

Appropriate polyethers or polyether groups can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, e.g., the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

While the art of preparing dental materials knows many different types of compounds, a typical curing mechanism is based either on polycondensation reactions of alkoxy silyl groups which might take place in the presence of an acidic catalyst or salt of a strong acid and water, or on polycondensation reactions of alkoxy silyl groups with silanol groups in the presence of a catalyst (preferably without water) or based upon a ring-opening polymerization e.g. of aziridines or based upon the polyaddition of silanes with olefinically unsaturated double bonds or based upon ring-opening metathesis reaction with unsaturated olefinically double bond.

It can be preferred, if the curing of the dental material is effected by compounds comprising aziridino groups, which are sometimes also referred to as ethylene imine groups.

The inventive dental compositions can thus comprise at least a component having on average at least 2 aziridino groups or more and a molecular weight of at least about 500.

The term "on average" is to be interpreted such in the context of the present text that a mixture of a large number of compounds may comprise both compounds having less than 2 aziridino groups and also compounds having more than 2 aziridino groups although, when seen over the entirety of the compounds of component (A), the average functionality of all molecules is, with respect to aziridino groups, 2 or more.

All mentioned types of polyaddition or polycondensation products can be provided with aziridino groups by means of any desired subsequent reactions known to the person skilled in the art. For example, it is possible first to introduce, into an appropriate polymer, substituents which are in turn capable of reacting with suitable aziridine derivatives. It is also possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised.

Suitable possible methods for providing the polymers with aziridino groups are mentioned, e.g., in DE 1 745 810 or DE 100 26 852 A1.

Suitable polymers can carry the aziridino groups terminally or laterally, or terminally and laterally, but preferably terminally.

The aziridino groups containing polymers typically have a dynamic viscosity η of from 10 to about 500 Pa*s, especially from about 15 to about 300 Pa*s. A preferred viscosity range is from about 20 to about 180 Pa*s at 23° C.

The aziridino equivalent is typically from about 250 to about 25,000 g/equivalent, especially from about 400 to about 10,000 g/equivalent.

A component (A) which can be used may comprise only one type of aziridino group containing polymer. It is, however, likewise possible for a component (A) to comprise two or more different types of aziridino polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

Suitable components include N-alkyl substituted aziridines attached to oligomeric and/or polymeric hydrocarbon, ester, ether or siloxane. The attached N-alkyl aziridene can be represented by the formula

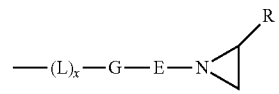

wherein
R represents H, C1-C12 alkyl, C2-C12 alkenyl, C2-C12 alkinyl, C7-C15 alkylaryl, C7-C15 arylalkyl, C3-C12 cycloalkyl, and wherein hydrogen atoms may be replaced by Cl or F and/or wherein up to five carbon atoms may be replaced by atoms or group of atoms selected from O, CO, N, S,
E represents a C1-C18 branched or unbranched hydrocarbon chain wherein up to five carbon atoms may be replaced by atoms or group of atoms selected from O, CO, N, S,
G represents a group selected from C(O)O, C(O)NR, C(O), C(O)C(O), C(O)(CH2)mC(O) with m=1 to 10, C(S)NR, CH2,
L represents O, S, NR with x=0 or 1.

In another embodiment of the invention, component (A) may comprise a system capable to be cured by hydrosilylation which consists of a component (A1) with at least two functional groups capable of reacting with a component (A2) which comprises SiH group(s) in the presence of a hydrosilation catalyst.

Thus, the curable polymer (A1) may comprise at least two pendant or terminal triorganosiloxy groups in which at least one of the three organic groups is a group with an ethylenically unsaturated double bond.

Generally, the groups with an ethylenically unsaturated double bond can be located on any monomeric unit of the polymer. It is, however, preferred, that the groups with an ethylenically unsaturated double bond are located on or at least near the terminal, monomeric units of the polymer chain.

In another embodiment, at least two of the groups with an ethylenically unsaturated double bond are located on the terminal monomeric units of the polymer chain of component (A1).

The term "monomeric units" as used throughout the present text relates to repeating structural elements in the polymer that form the polymer backbone, unless expressly stated otherwise.

The inventive composition may further comprise as component (A2) a crosslinker compound containing at least two or three SiH groups.

By definition, an organohydrogenpolysiloxane according to the present text does not belong to the group of organopolysiloxanes used as component (A1) or part of component (A1) as described in the context of the invention.

An organohydrogenpolysiloxane according to the invention typically contains from about 0.01 to about 1.7 wt.-% silicon-bonded hydrogen or from about 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least about 50%, preferably about 100%, of the hydrocarbon radicals R that are bonded to silicon atoms are methyl radicals.

Organohydrogenpolysiloxanes which can be suitable as component (A2) include those having a viscosity of about 10 to about 1,000 mPas or from about 15 to about 550 mPas or from about 20 to about 150 mPas.

In an alternative embodiment, the dental composition may employ a curable polymer composition based on a condensation curing of a condensation curable polymer. Condensation curable organopolysiloxanes have been described e.g. in DE 41 37 698 (corresponding to U.S. Pat. No. 5,597,882).

Examples of dental compositions based on a condensation curable silicone polymer include as component (A1) of the curable composition a polydialkylsiloxane having at least two hydroxy groups and as component (A2) a silane compound having two or more hydrolysable groups such as for example alkoxy groups.

An example of a suitable polysiloxane having two or more hydroxy groups includes polydialkylsiloxanes, for example polydimethylsiloxane, that are terminated with a hydroxy group at both opposite ends of the polymer chain. Generally, the hydroxyl terminated polydialkylsiloxanes may have a molecular weight (Mn) of about 900 to 500,000, for example between 1500 and 150,000 g/mol.

Suitable silane compounds having two or more hydrolysable groups include in particular esters of silic acid, esters of polysilic acid and polysiloxanes having two or more alkoxy groups bound to a silicium atom. Typical examples include compounds according to the formula:

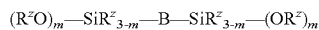
$(R^zO)_m$—$SiR^z_{3-m}$—B—$SiR^z_{3-m}$—$(OR^z)_m$

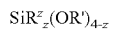
$SiR^z_z(OR')_{4-z}$

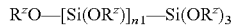
$R^zO$—$[Si(OR^z)]_{n1}$—$Si(OR^z)_3$ wherein in the above formula B represents the divalent group of formula —O—$(SiR_2$—$O)_{m2}$— with R representing an aromatic or aliphatic hydrocarbon group which may optionally be substituted and m2 represents a value of 10 to 6000, R' and $R^z$ independently represents an alkyl group (e.g. C1 to C4) or an aryl group that may be substituted, n1 represents a value of 1 to 100, m is an integer of 1 to 3 and z is 0, 1 or 2.

In another embodiment of the invention, the component A can be composed of an alkoxy-functional polyether and optionally an hydroxysilyl-functional polyether as, e.g. described in U.S. Pat. No. 7,504,442 B2, EP 1 722 741 B1, EP 1 402 873 B1 or EP 0 269 819 B1 or may be a mixture polyether and organopolysiloxane components.

In an alternative embodiment, the dental composition may employ a curable polymer composition based on a ring-opening metathesis curing (ROMP) of a ROMP curable polymer. ROMP curable organopolysiloxanes or polyethers for dental application have been described in for example EP 1 317 914 A1 (corresponding to U.S. Pat. No. 6,649,146).

Reactive groups capable for ROMP reaction with e.g. ruthenium catalysts are for example cycloalkenyl groups, such as norbornyl and cyclopentenyl groups. The composition contains a curable polymer having at least two cycloalkenyl groups. The reactive groups can be connected to the polymeric backbone by functional group, as e.g. silyl, ether or ester groups.

The inventive composition also contains an initiator as component (B) capable of initiating a curing reaction of component (A).

The amount of the component (B) to be used is not particularly limited, unless the desired curing reaction cannot be initiated or catalyzed.

Component (B) is typically present in an amount of at least about 0.0001 wt.-% or at least about 0.0005 wt.-%, wt.-% with respect to the whole composition.

Component (B) is typically present up to an amount of about 35 wt.-% or up to about 20 wt.-%, wt.-% with respect to the whole composition.

Typical ranges include from about 0.0001 wt.-% to about 35 wt.-% or from about 0.0005 wt.-% to about 20 wt.-% (wt.-% with respect to the weight of the whole composition).

Depending on the reactive moieties being present in component (A) different initiators have to be used.

If component (A) comprises moieties which can react via a ring-opening reaction, especially via a ring-opening reaction of aziridino groups containing components, the following initiators were found to be useful:

As initiator substances there come into consideration, in principle, all compounds triggering the polymerisation of aziridines, provided that they bring about a suitable setting rate and suitable elastomeric properties for the cured dental material.

Accordingly, for use in two-component impression materials comprising a curable polyether group containing polymer or derivative described hereinbefore there are suitable those initiator substances which make possible curing of the mixed preparation at room temperature in a period of from about 1 to about 20 minutes to form a resilient solid body, that solid body meeting the requirements for a resilient impression material according to DIN/EN 2482 and having a Shore A hardness (DIN 53 505) of at least 20 after 24 hours.

Sulfonium salts, especially alkyl sulfonium salts or sulfonium salts derived from glutaconic acid were found to be useful. Those and others are described e.g. in WO 2007/016295, U.S. Pat. No. 4,167,618, DE 914 325 and DE 100 18 918 A1, the content of which in regard to initiators is explicitly mentioned and herewith incorporated by reference.

Trialkylsulfonium salts as are described in, for example, U.S. Pat. No. 4,167,618 (e.g.: column 2, line 36-column 4, line 32 and Examples) are especially suitable as initiator substances. The mentioned trialkylsulfonium salts are understood as being part of the disclosure of the present text.

In DE 914 325, the use of oxonium, ammonium and sulfonium salts as initiator substances is proposed (e.g.: p. 2, line 77-p. 3, line 100 and Examples), the initiator substances mentioned therein likewise being considered part of the disclosure of the present text.

In DE 100 18 918 A1, initiators are described which impart just a low degree of acidity to the catalyst component and which make possible a readily adjusted, relatively long processing time after mixing of the basic component and catalyst component has been carried out. Reference is expressly made also to the compounds mentioned therein and the initiator substances mentioned therein are likewise considered part of the disclosure of the present text.

In the context of the invention, the following initiator compounds are preferably used: zinc salt of p-toluenesulfonic acid, β-(S-lauryl-S-ethylsulfonium)butyronitrile tetrafluoroborate, dodecylbenzenesulfonic acid zinc salt, β-(S-lauryl-S-ethylsulfonium)-β-phenylacrylic acid butyl ester tetrafluoroborate.

A further preferred class of initiators can be classified as sulfonium salts or derivatives of glutaconic acid esters as describe in WO 2007/016295.

Typical ranges for these kinds of initiators include from about 1 wt.-% to about 50 wt.-% or from about 3 wt.-% to about 40 wt.-% from about 4 wt.-% to about 25 wt.-%, wt.-% with respect to the weight of the whole composition.

The molar ratio between the initiator and the polyether group containing polymer curable by a ring-opening reaction, e.g. a polyether group containing polymer comprising aziridine groups includes ranges from about 1.0:0.1 to about 1.0:20.0, or from about 1.0:0.5 to about 1.0:10.0, or from about 1.0:0.8 to about 1.0:30.

If component (A) comprises moieties which can react via a hydrosilation reaction, a suitable catalyst or initiator is typically a platinum catalyst or a platinum containing catalyst, including a platinum complex which can be prepared from hexachloroplatinum acid by reduction with tetramethyldivinyldisiloxane. Such compounds are known to the skilled person. Any other compounds which catalyze or accelerate addition cross-linking of silanes with ethylenically unsaturated double bonds are also suitable. Platinum-siloxane complexes as described, e.g. in U.S. Pat. No. 3,715,334, U.S. Pat. No. 3,775,352 and U.S. Pat. No. 3,814,730 are suitable. The disclosure of these patents with regard to platinum complexes and their preparation is explicitly mentioned and expressly regarded as part of the disclosure of the present text.

Typical ranges for these kinds of initiators include from about 0.00005 to about 0.05 wt.-%, or from about 0.0002 to about 0.04 wt.-%, each calculated as elemental platinum and related to the overall weight of the composition.

If component (A) comprises moieties which can cure via a condensation reaction, suitable catalyst or initiator include organo zinc compounds, titanates, zirconates such as for example tetraethyltitanate, tetraisopropyltitanate, tetra-n-propyltitanate, tetra-n-butyltitanate, dioctylzincdilaurate, dibutylzincdilaurate, tetra-n-butylzirconate and tetra-n-propylzirconate.

Typical ranges for these kinds of initiators include from about 0.005 wt.-% to about 35 wt.-% or from about 0.01 wt.-% to about 20 wt.-%, wt.-% with respect to the weight of the whole composition.

If component (A) comprises moieties which can cure via a ROMP reaction with catalyst known to the person skilled to the art. Suitable catalyst or initiator include ruthenium carbene complexes, e.g. the Hoveyda-Grubbs catalyst as well as Schrock catalysts based on tungsten or molybden complexes.

Typical ranges for these kinds of initiators include from about 0.0001 wt.-% to about 1 wt.-% or from about 0.001 wt.-% to about 1 wt.-%, wt.-% with respect to the weight of the whole composition.

The curable dental composition of the invention comprises an F— containing compound as component (C).

The F-containing compound(s) used in the composition of the invention can be simple compounds, polymeric or oligomeric. When the F-containing compound is oligomeric of polymeric, it can be a homopolymer or copolymer. Suitable copolymeric structures include block-copolymers, alternating or statistic polymers as well as random copolymers.

The composition comprises an F-containing compound having generally a linear or branched backbone. The per- or partly fluorinated backbone of the F-containing compound is typically interrupted by one or more oxygen atoms.

Furthermore, certain embodiments of the F-containing compound can be characterized by one or more of the following features:

Chain-length of the backbone: more than about 8 atoms and less than about 100, for example not more than 50, for example less than 36 atoms (atoms counted along the longest chain in the molecule without taking into account the end groups T, $G^1$ and $G^2$ in the above formulas.

Containing 1 to about 10 or 2 to about 8 or 2 to about 6 ether structure elements.

Containing at least one, two, three, four, five, six, seven or eight oxygen atom(s) connecting per- or partly fluorinated elements selected from $CF_3$—, —CHF—, —$CF_2$—, $CF_3$—$CF_2$—, —$CF_2$—$CF_2$—, —CHF—$CF_2$—, $CF_3$—CHF—, $CF_3$—$CF_2$—$CF_2$—, —$CF_2$—$CF_2$—$CF_2$—, —$CF(CF_3)$—$CF_2$—, —$CF(CF_3)$—, —$CF_3$—$CF_2$—$CF_2$—$CF_2$—, $CF_3$—$CF_2$—$CF_2$—$CF_2$—.

The terminal groups in the molecule can be a perfluor or partly fluorinated linear or branched alkyl chain (e.g. C1-C6), a fluorine atom, an alcohol, an ether functionality or an ester functionality, wherein both terminal groups can be equal or different. The preferred esters or ethers are typically based on linear or branched C1-C9 alkyl chains, C1-C9 aryl residues or C1-C9 alkylaryl residues.

The per- or partly fluorinated chain-segments of the main-chain do typically not comprise more than 5 atoms in a row.

The F-containing compound is preferably a low molecular compound with a molecular weight (Mn) equal or below about 3000 g/mol or equal or below about 2000 g/mol.

Typically, the molecular weight (Mn) is above about 200 or above about 250 or above about 300. Thus, the molecular weight of the F-containing compound is typically within a range of about 200 to about 3000 or about 250 to about 2500 or about 300 to about 2000. In a particularly preferred embodiment, the number average molecular weight is less than 3000 g/mol or not more than 1800 g/mol and the fraction of molecules have a molecular weight of 750 g/mol or less is not more than 10% by weight or not more than 5% by weight based on the total weight of F-containing compound.

The amount of the component (C) to be used is not particularly limited, unless the desired effect or effects (e.g. improving the de-gassing behaviour and/or the hydrophilicity of the curable composition) cannot be achieved.

Typically, the F-containing compound is present in the curable composition in an amount of about 0.1 to about 7.5 wt.-% or about 0.2 to about 5 wt.-% with respect to the whole composition.

If the composition is provided as a kit of parts comprising a base paste and a catalyst paste, the F-containing compound can be present either in the base paste or the catalyst paste or in the base paste and the catalyst paste.

If the F-containing compound is present in the base paste, it is typically present in an amount of about 0.1 to about 7.5 wt.-% or about 0.2 to about 5 wt.-% or about 0.3 to about 5 wt.-% with respect to the whole weight of the base paste.

If the F-containing compound is present in the catalyst paste, it is typically present in an amount of about 0.1 to about 7.5 wt.-% or about 0.2 to about 5 wt.-% or about 0.3 to about 5 wt.-% with respect to the whole weight of the catalyst paste.

According to another embodiment of the invention the fluor-content of the F-containing compound can be in a range of about 10 to about 90 wt.-% or about 40 to about 70 wt.-% with respect to the molecular weight (Mn) of the F-containing compound.

Specific examples of the F-containing compound include:
Rf—$(O)_t$—CHF—$(CF_2)_x$-T, with t=0 or 1, x=0 or 1 and Rf being a linear or branched per- or partly fluorinated alkyl chain (including C1 to C6 or C1 to C4), wherein the alkyl chain can be interrupted by O atoms, with the proviso that when t is 0, the Rf group is a linear or branched per- or partly fluorinated alkyl chain (including C1 to C6 or C1 to C4) interrupted by one or more O atoms Rf—$(OCF_2)_m$—O—$CF_2$-T, with m=1 to about 6 and Rf being a linear or branched per- or partly fluorinated alkyl chain (including C1 to C6 or C1 to C4), wherein the alkyl chain can be interrupted by O atoms, $CF_3$—$(CF_2)_2$—$(OCF(CF_3)$—$CF_2)_z$—O-L-T, with z=0, 1, 2, 3, 4, 5, 6, 7 or 8, L having a structure selected from —$CF(CF_3)$—, —$CF_2$—, —$CF_2CF_2$— and —$CHFCF_2$, Rf—$(O$—$CF_2CF_2)_n$—O—$CF_2$-T, with n=1, 2, 3, 4 or 5 and Rf being a linear or branched per- or partly fluorinated alkyl chain (including C1 to C6 or C1 to C4), wherein the alkyl chain can be interrupted by O atoms, an oligomeric compound obtainable by the anionic or photochemical (in the presence of oxygen) polymerization or copolymerisation of monomers selected from vinylidenfluoride, hexafluoropropylenoxide, tetrafluoroethylene, 2,2,3,3-tetrafluorooxetane, trifluoroethylene or monofluoroethylene, wherein at least one chain-end of the oligomeric compound is represented by a function T, T being selected from the group consisting of —COOR, —$CONR^bR^c$—$CH_2OH$, —$CF_2OR$, —CHFOH, —CHFOR, —$CH_2OR$ or —F with R and being a linear or branched alkyl chain (C1 to C9), aryl chain (C1 to C9) or alkylaryl chain (C1 to C9) each of which may optionally be substituted with one or more substituents selected from the group consisting of hydroxyl, amino group, halogen atom, an SiH group and a group capable of reacting with SiH, $R^b$ and $R^c$ independently representing H or having a meaning as given for R.

Specific examples of oligomeric compounds include
a) homo- or copolymerization of hexafluoropropylenoxide and/or 2,2,3,3-tetrafluorooxetane
b) homo- or copolymerization of vinylidenfluoride, hexafluoropropylenoxide, tetrafluoroethylene, 2,2,3,3-tetrafluorooxetane, trifluoroethylene and/or monofluoroethylene in the presence of oxygen In particular, the esters, especially the methylesters, and the amidols (T=C(O)NH-alkyl-OH) and the respective alcohols or methylethers, prepared by chemical reduction, of the following structures can be used. Specific examples of F-containing compounds, which can be used, include those listed below:

Rf—O—CHF-T, with Rf being a linear or branched per- or partly fluorinated alkyl chain (including C1 to C6), which can be interrupted by oxygen atoms.

Specific examples according to the above formula include:
$CF_3$—O—$CF_2$—O—$CF_2$—$CF_2$—O—CHF-T
$CF_3$—$(O$—$CF_2)_2$—O—$CF_2$—$CF_2$—O—CHF-T
$CF_3$—$(O$—$CF_2)_3$—O—$CF_2$—$CF_2$—O—CHF-T Rf—O—CHF—$CF_2$-T, with Rf being a linear or branched per- or partly fluorinated alkyl chain (including C1 to C6), which can be interrupted by oxygen atoms.
$CF_3$—O—$CF_2$—O—$CF_2$—$CF_2$—O—CHF—$CF_2$-T
$CF_3$—$(O$—$CF_2)_2$—O—$CF_2$—$CF_2$—O—CHF—$CF_2$-T
$CF_3$—$(O$—$CF_2)_3$—O—$CF_2$—$CF_2$—O—CHF—$CF_2$-T $R_f$—O—$CF_2$—CHF-T, with Rf being a linear or branched per- or partly fluorinated alkyl chain (including C1 to C6), which can be interrupted by oxygen atoms.

Specific examples according to the above formula include:
$C_3F_7$—O—$CF_2$—CHF-T
$CF_3$—O—$CF_2$—O—$CF_2$—$CF_2$—O—$CF_2$—CHF-T
$CF_3$—$(O$—$CF_2)_2$—O—$CF_2$—$CF_2$—O—$CF_2$—CHF-T
$CF_3$—$(O$—$CF_2)_3$—O—$CF_2$—$CF_2$—O—$CF_2$—CHF-T Rf—O—$CF_2$—CHF—$CF_2$-T, with Rf being a linear or branched per- or partly fluorinated alkyl chain (including C1 to C6), which can be interrupted by oxygen atoms.

Specific examples according to the above formula include:
$C_3F_7$—O—$CF_2$—CHF—$CF_2$-T
$CF_3$—O—$CF_2$—$CF_2$—$CF_2$—O—$CF_2$—CHF—$CF_2$-T
$CF_3$—O—$CF_2$—O—$CF_2$—$CF_2$—O—$CF_2$—CHF—$CF_2$-T
$CF_3$—$(O$—$CF_2)_2$—O—$CF_2$—$CF_2$—O—$CF_2$—CHF—$CF_2$-T
$CF_3$—$(O$—$CF_2)_3$—O—$CF_2$—$CF_2$—O—$CF_2$—CHF—$CF_2$-T $R_f$—O—$CF_2$—$CF_2$-T, with Rf being a linear or branched per- or partly fluorinated alkyl chain (including C1 to C6), which can be interrupted by oxygen atoms, n=1, 2 or 3 and m=0 or 1.

Specific examples according to the above formula include:
$CF_3$—O—$CF_2$—$CF_2$-T
$C_2F_5$—O—$CF_2$—$CF_2$-T
$C_3F_7$—O—$CF_2$—$CF_2$-T
$C_4F_9$—O—$CF_2$—$CF_2$-T Rf—$(O$—$CF_2)_u$—O—$CF_2$-T, with Rf being a linear or branched per- or partly fluorinated alkyl chain (including C1 to C6), which can be interrupted by oxygen atoms, and u=1, 2, 3, 4, 5 or 6.

Specific examples according to the above formula include:
$CF_3$—$(O$—$CF_2)_3$—O—$CF_2$-T
$CF_3$—$(O$—$CF_2)_5$—O—$CF_2$-T Rf—$(O$—$CF_2$—$CF_2)_k$—O—$CF_2$-T, with Rf being a linear or branched per- or partly fluorinated alkyl chain (including C1 to C6), which can be interrupted by oxygen atoms and k=1, 2, 3, 4, 5.
$C_2F_5$—$(O$—$CF_2$—$CF_2)_1$—O—$CF_2$-T
$C_3F_7$—$(O$—$CF_2$—$CF_2)_1$—O—$CF_2$-T
$C_4F_9$—$(O$—$CF_2$—$CF_2)_1$—O—$CF_2$-T
$C_2F_5$—$(O$—$CF_2$—$CF_2)_2$—O—$CF_2$-T
$CF_3$—$(O$—$CF_2$—$CF_2)_2$—O—$CF_2$-T
$C_3F_7$—$(O$—$CF_2$—$CF_2)_2$—O—$CF_2$-T
$C_4F_9$—$(O$—$CF_2$—$CF_2)_2$—O—$CF_2$-T Rf—O—$CF_2$-T, with Rf being a linear or branched per- or partly fluorinated alkyl chain (including C1 to C6), which can be interrupted by oxygen atoms.

Specific examples according to the above formula include:
$C_3F_7$—O—$CF_2$-T
$CF_3$—$(CF_2)_2$—$(O$—$CF(CF_3)$—$CF_2)_z$—O—$CF(CF_3)$-T
with z=0, 1, 2, 3, 4, 5, 6, 7 or 8, Specific examples according to the above formula include:
$CF_3—(CF_2)_2—(O—CF(CF_3)—CF_2)_2—O—CF(CF_3)$-T
$CF_3—(CF_2)_2—(O—CF(CF_3)—CF_2)_3—O—CF(CF_3)$-T
$CF_3—(CF_2)_2—(O—CF(CF_3)—CF_2)_4—O—CF(CF_3)$-T
$CF_3—(CF_2)_2—(O—CF(CF_3)—CF_2)_5—O—CF(CF_3)$-T
$CF_3—(CF_2)_2—(O—CF(CF_3)—CF_2)_z—O—CF(CF_3)$—
 $CONHCH_2CH_2OH$
$CF_3—(CF_2)_2—(O—CF(CF_3)—CF_2)_z—O—CF(CF_3)$—
 $CONHCH_2CH_2O—Si(CH_3)_2—CH=CH_2$
$CF_3—CHF—O—(CF_2)_o$-T, with o=1, 2, 3, 4, 5 or 6.
Specific examples according to the above formula include:
$CF_3—CFH—O—(CF_2)_3$-T
$CF_3—CFH—O—(CF_2)_5$-T
$CF_3—CF_2—O—(CF_2)_o$-T, with o=1, 2, 3, 4, 5 or 6.
Specific examples according to the above formula include:
$CF_3—CF_2—O—(CF_2)_3$-T
$CF_3—CF_2—O—(CF_2)_5$-T.

T-$CF_2—O—(CF_2—CF_2—O)_p—(CF_2—O)_q—CF_2$-T, with p/q=about 0.5 to about 3.0 and an molecular weight in the range of about 500 to about 4000 g/mol.

T-$CF_2—(O—CF(CF_3)—CF_2)_n—(O—CF_2)_m—O—CF_2$-T with n/m=about 20 to about 40 and a molecular weight in the range of about 650 to about 3200 g/mol.

Rf—$(O—CF_2—CF_2—CF_2)_n—O—CF_2—CF_2$-T with n=1-25 and Rf being a linear or branched per- or partly fluorinated alkyl chain (including C1 to C6), wherein the alkyl chain can be interrupted by O atoms.

In the above formulas T is selected from the group consisting of —COOR, —CONR$^b$R$^c$, —CH$_2$OH, —CF$_2$OR, —CHFOH, —CHFOR, —CH$_2$OR or —F with R and being a linear or branched alkyl chain (C1 to C9), aryl chain (C1 to C9) or alkylaryl chain (C1 to C9) each of which may optionally be substituted with one or more substituents selected from the group consisting of hydroxyl, amino group, halogen atom, an SiH group and a group capable of reacting with SiH, R$^b$ and R$^c$ independently representing H or having a meaning as given for R.

Suitable fluorinated compounds for use in connection with the present invention include fluorinated polyethers that are commercially available under the tradename FOMBLIN™, GALDEN™ and H-Galden™, Fluorolink™ materials or may be prepared using preparation methods described in US2007/0276068, EP 870877, WO 2004/060964, WO 2007/140091, US 2007/015864, US 2007/015864, US 2007/025902 and US 2007/015937.

HFPO can be obtained as described in U.S. Pat. No. 3,242,218 or US 2004/0124396. The general formula of a methyl ester derivative of HFPO is $C_3F_7O[CF(CF_3)CF_2O]_nCF(CF_3)COOCH_3$ with n being 1 to 8.

In contrast to the F-containing compound of the present invention, the F-containing compounds used e.g. in U.S. Pat. No. 4,657,959, GB 2,337,524 or WO 2007/080071 for example do not contain a group R$_f$ which is a partially or fully fluorinated aliphatic group interrupted by one or more oxygen atoms. The F-containing compounds referred to in those references contain perfluorated alkyl groups.

The curable dental composition of the invention may also include one Si-containing surfactant or mixture of Si-containing surfactants as component (D1).

There is no need for component (D1) to be present, however, if component (D1) is present, it is typically present in an amount of at least about 0.05 wt.-% or at least about 0.1 wt.-% or at least about 0.5 wt.-%.

Component (D1) is typically present up to an amount of about 5 wt.-% or up to about 6 wt.-% or up to about 7 wt.-%.

Typical ranges include from about 0 wt.-% to about 7 wt.-% or from about 0.1 wt.-% to about 6 wt.-% from about 0.5 wt.-% to about 5 wt.-%.

If component (D1) is present it is typically present in an amount sufficient and not detrimental to the desired effect or effects to be achieved (e.g. improving the de-gassing behaviour and/or the hydrophilicity of the curable composition).

Surfactants or hydrophilizing agents which can be employed can generally be chosen freely from all types of surfactants which improve the hydrophilicity of a polyether group containing polymer.

Preferably, the use of the surfactant should not negatively impact the material properties or curing behavior of the curable composition or at least not more than avoidable or tolerable.

Component (D1) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state) over that wetting angle achieved on the same composition without component (D1).

In certain embodiments, the surfactant does not contain reactive groups so that it is not incorporated into the network of the hardenable composition.

According to one embodiment of the invention, the molar ratio of F-containing compound to surfactant, if used, can be in a range of about 0.05 to about 4 or about 0.08 to about 2.4 or about 0.1 to about 1.8.

Useful surfactants include polyether carbosilanes of the general formula Q-P—$(OC_nH_{2n})_x$—OZ, in which Q stands for $R_3Si$— or $R_3Si$—$(R'—SiR_2)_a$—$R'$—$SiR''_2$—
where every R in the molecule can be the same or different and stands for an aliphatic C1-C18, a cycloaliphatic C6-C12 or an aromatic C6-C12 hydrocarbon radical, which can optionally be substituted by halogen atoms, R' is a C1-C14 alkylene group, R" is R in the case of a≠0 or is R or $R_3SiR'$ in the case of a=0, and a=0-2; P stands for a C2-C18 alkylene group, preferably a C2-C14 alkylene group or A-R''', where A represents a C2-C18 alkylene group and R''' a functional group selected from: —NHC(O)—, —NHC(O)—$(CH_2)_{n-1}$—, —NHC(O)C(O)—, —NHC(O)$(CH_2)_v$C(O)—, —OC(O)—, —OC(O)—$(CH_2)_{n-1}$—, —OC(O)C(O)—, —OC(O)(CH$_2)_v$C(O)—, —OCH$_2$CH(OH)CH$_2$OC(O)(CH$_2)_{n-1}$—, —OCH$_2$CH(OH)CH$_2$OC(O)(CH$_2)_v$C(O)—
with v=1-12; Z is H or stands for a C1-C4 alkyl radical or a C1-C4 acyl radical; x stands for a number from 1 to 200 and n stands for an average number from 1 to 6, preferably 1 to 4. Thus, the element —SiR"$_2$— can also comprise the substructure —Si(R)(R$_3$SiR')—.

The polyether part can be a homopolymer, but can also be a statistical, alternating or block copolymer.

Also possible is the use of polyether carbosilanes selected from the group consisting of:
Et$_3$Si—(CH$_2)_3$—O—(C$_2$H$_4$O)y-CH$_3$, Et=Ethyl
Et$_3$Si—CH$_2$—CH$_2$—O—(C$_2$H$_4$O)y-CH$_3$, Et=Ethyl
(Me$_3$Si—CH$_2)_3$Si—(CH$_2)_3$—O—(C$_2$H$_4$O)y-CH$_3$, Me=Methyl
Me$_3$Si—CH$_2$—SiMe$_2$-(CH$_2)_3$—O—(C$_2$H$_4$O)y-CH$_3$, Me=Methyl
(Me$_3$Si—CH$_2)_2$SiMe-(CH$_2)_3$—O—(C$_2$H$_4$O)y-CH$_3$, Me=Methyl
Me$_3$Si—(CH$_2)_3$—O—(C$_2$H$_4$O)y-CH$_3$, Me=Methyl
Me$_3$Si—CH$_2$—CH$_2$—O—(C$_2$H$_4$O)y-CH$_3$, Me=Methyl
Ph$_3$Si—(CH$_2)_3$—O—(C$_2$H$_4$O)y-CH$_3$, Ph=phenyl
Ph$_3$Si—CH$_2$—CH$_2$—O—(C$_2$H$_4$O)y-CH$_3$, Ph=phenyl Cy₃Si—(CH₂)₃—O—(C₂H₄O)y-CH₃, Cy=cyclohexyl
Cy₃Si—CH₂—CH₂—O—(C₂H₄O)y-CH₃, Cy=cyclohexyl
(C₆H₁₃)₃Si—(CH₂)₃—O—(C₂H₄O)y-CH₃
(C₆H₁₃)₃Si—CH₂—CH₂—O—(C₄H₄O)y-CH₃ in which y conforms to the relation: 5≤y≤20.

Surfactants which can also be used, either alone or as a mixture of two or more thereof, can be found in U.S. Pat. No. 5,750,589 (Zech et al), col. 2, l. 47 to col. 3 l. 27 and col. 3, l. 49 to col. 4, l. 4 and col. 5, l. 7 to col. 14, l. 20.

Other surfactants which can be used, either alone or as a mixture of two or more thereof, can be found in U.S. Pat. No. 4,657,959 (Bryan et al.), col. 4, l. 46 to col. 6. l. 52 as well as in EP 0 231 420 B1 (Gribi et al.) p 4, l. 1 to p. 5, l. 16 and in the examples.

U.S. Pat. No. 5,750,589, U.S. Pat. No. 4,657,959 and EP 0 231 420 B1 are expressly described and cited herein as a source of disclosure for compounds which can be used as component (D1) according to the invention.

Some of the surfactants, which can be used as component (D1) or part of component (D1) can be summarized under the following formula

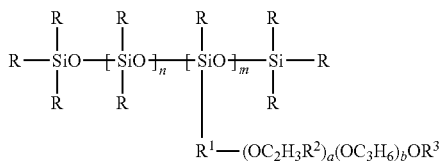

where each R is independently a monovalent hydrocarbyl radical with 1 to 22 C-atoms, R¹ is a divalent hydrocarbylene radical 1 to 26 C-atoms, each R² is independently hydrogen or a lower hydroxyalkyl radical, R³ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and R³ are —CH₃, R¹ is —C₃H₆—, R² is hydrogen, n is about zero or about one, m is about one to about five, a is about five to about 20 and b is about 0.

Several of such ethoxylated surfactants are for example available from Momentive Performance Materials Inc. including "SILWET™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and R³ are —CH₃, R¹ is —C₃H₆—, R² is hydrogen, n is about zero or about one, m is about one or about two, a is about seven, and b is about 0. Also possible is the use of MASIL™ SF19, as obtainable from Lubrizol performance products, Spartanburg, US.

The curable dental composition of the invention may also include a hydrocarbon surfactant or mixture of surfactants as component (D2).

The inventive composition is typically obtained by mixing a base paste and a catalyst paste. In this respect, the surfactant can be present in the base paste or the catalyst paste, or in the base paste and the catalyst paste. In one embodiment of the invention, the surfactant is present in the base paste only.

There is no need for component (D2) to be present, however, if component (D2) is present, it is typically present in an amount of at least about 0.05 wt.-% or at least about 0.01 wt.-% or at least about 0.1 wt.-%.

Component (D2) is typically present up to an amount of about 10 wt.-% or up to about 15 wt.-% or up to about 20 wt.-%.

Typical ranges include from about 0 wt.-% to about 20 wt.-% or from about 0.01 wt.-% to about 15 wt.-% from about 0.1 wt.-% to about 10 wt.-%.

If component (D2) is present it is typically present in an amount sufficient and not detrimental to the desired effect or effects to be achieved (e.g. improving the de-gassing behaviour and/or the hydrophilicity of the curable composition).

Useful surfactants, which can improve the hydrophilicity of a polyether group containing polymer according to the invention, can generally be chosen from anionic, cationic or non-ionic surfactants or mixtures of two or more of such types of surfactants.

Examples of useful non-ionic surfactants include those according to the formula:

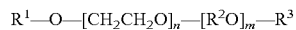

wherein R¹ represents hydrogen or an aromatic or aliphatic, linear or branched hydrocarbon group having 1-20 carbon atoms, R² represents an alkylene having 3 carbon atoms, R³ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8.

Still further examples include those in which R¹ in the above formula represents an alkyl group of 4 to 20 carbon atoms, m is 0 and R³ is hydrogen. An example thereof includes isotridecanol ethoxylated with about 8 ethoxy groups and which is commercially available as GENAPOL™ X080 from Clariant GmbH.

Non-ionic surfactants according to the above formula with R¹ and R³ representing a C1-C3 alkyl chain or hydrogen and in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or PluroniC™.

In a particular embodiment of the present invention, a mixture of a Si-containing surfactant, for example a Si-surfactant as exemplified above as component (D1), and one or more non-ionic surfactants selected from hydrocarbon surfactants as described above as component (D2) can be used.

This combination was found to be particular useful not only to improve the de-gassing behaviour but also to improve the hydrophilicity of the curable dental composition.

According to another embodiment, the inventive composition may contain a filler or a mixture of fillers, e.g. as component (E) or as a part of component (E), even if the presence of a filler is not mandatory. The nature of the filler is not particularly limited, either.

Typically filler can be used in an amount of from of at least about 0.1 wt.-% or at least about 0.2 or at least about 0.5 wt.-% with respect to the whole composition.

There is no particular upper limit, however, typically the amount of filler, if present at all, is used in an amount of at most about 80 wt.-% or at most about 75 wt.-% or at most about 70 wt.-% with respect to the whole composition.

Thus, typical ranges for the filler as component (F) include from about 0 to about 80 or from about 0.2 to about 75 or from about 0.5 to about 70 wt.-% with respect to the whole composition.

A wide variety of inorganic, hydrophilic or hydrophobic fillers may be employed such as silicas, aluminas, magnesias, titanias, inorganic salts, metallic oxides and glasses. It has been found to be possible to employ mixtures of silicone dioxides, such as a diatomaceous earth and/or fumed silica. Those filler are commercially available from companies like Cabot Corporation, Wacker or Degussa under the trade names Aerosil™, HDK-H, Cab-o-Sil.

More specifically, fillers which can be used include calcium silicate, diatomaceous earth, zirconium silicate, montmorillonite such as bentonite, zeolite, including molecular sieves such as sodium aluminium silicate, barium sulphate, calcium carbonate, plaster, glass and plastic powder.

The sizes and surface areas of the foregoing materials can be adjusted to control the viscosity and thixotropicity of the resulting compositions. The particle distribution is preferably chosen such that there are no fillers with particle sizes of more than about 50 µm.

A combination of reinforcing and non-reinforcing fillers can be preferred. In this respect, the quantity of reinforcing fillers can range from about 0 to about 10 wt.-%, in particular from about 0.2 to about 7 wt.-% with respect to the whole composition.

Typical reinforcing fillers include fumed silica, carbon black and the like. They also can improve mechanical properties like tensile strength or tear strength, of the cured silicone composition.

Typical non-reinforcing fillers are precipitated silicas, diatomaceous earth, aluminas, magnesias, titanium dioxide, zirconium silicate, and the like.

According to a further embodiment, the composition can also contain one or more additives as component (F) or part of component (F).

There is no need for additive(s) (F) to be present, however, if additive(s) (F) are present, they are typically present in an amount of at least about 0.005 wt.-% or at least about 0.01 wt.-%.

Component (F) can be present up to an amount of about 50 wt.-% or up to about 40 wt.-% or up to about 35 wt.-%.

Typical ranges include from about 0 wt.-% to about 50 wt.-% or from about 0.005 wt.-% to about 40 wt.-% from about 0.01 wt.-% to about 35 wt.-%.

If additive(s) are present, they are typically present in an amount sufficient and not detrimental to the desired effect or effects to be achieved (e.g. improving the de-gassing behaviour and/or the hydrophilicity of the curable composition).

Additives include retarders to modify the working and setting time, rheology modifier(s), thixotropic agent(s), diluting agent(s), inhibitor(s), pigment(s), dye(s), plastizer(s), odorous substance(s), flavouring(s), stabilizer(s), anti oxidant(s) alone in admixture or combination.

All kinds of known and compatible softeners and rheology modifiers like non reactive polymeric fluids or fats commonly used in commercialized impression materials can be added as well as pigments and stabilizers of any kind.

Preferred are those ingredients and additives that do not add unpleasant smell or taste. Compounds that have an unpleasant smell might be removed by thin film evaporation, if needed.

Typical plasticisers include, e.g., compounds of the ester type such as C12- to C15-alkyl lactates, ethyl or butyl esters of citric acid or of acetylcitric acid, phthalic acid esters of relatively long, branched alcohols such as bis(2-ethylhexyl) phthalate or phthalic acid polyester, C2- to C22-dialkyl esters of C2- to C6-dicarboxylic acids such as bis(2-ethylhexyl) adipate, dioctyl maleate, diisopropyl adipate, aromatic and aliphatic sulfonic acid esters such as C2- to C20-alkylsulfonic acid esters of phenol or of C1- to C22-alkanols or typical aromatic plasticisers such as polyphenyls in a wide viscosity range, including wax-like polyphenyls such as are obtainable, for example, from the Monsanto company, isomeric mixtures of C20 to C40 aromatic compounds, with preference being given to the use of mixtures of plasticisers of the ester type and aromatic type.

Liquids such as C12-C15 alkyl acetates, liquid derivatives of citric acid, esters of phthalic acid with branched alcohols like bis(2-ethylhexyl)phthalate or polymeric phthalates, C2-C18 bis(alkyl)esters of C2-C6 dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, xylyl toluene, and dixylyl toluene can be used. Also low molecular weight alcohols that may contain more than one OH-function like propane-1,2-diol may be used. From the group of polymeric compounds, polypropylene glycols and its derivatives are sometimes preferred.

Suitable diluting agent(s) usually do not contain reactive moieties like —SH or —COOH, primary or secondary amino groups, but may contain —OH.

An example of a preferred plasticiser mixture is a mixture of acetyl tributyl citrate and dibenzyltoluene.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in DE 197 11 514 A1 (e.g. p. 2, line 65-p. 3, line 22), to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopädie der industriellen Chemie", 4th edition, volume 11, p. 469.

Mixtures of naturally occurring fats, and also synthetically prepared fats such as Softisan™ 154 or Dynasan™ 118 (from Hüls Comp.) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula:

R2-O—CH$_2$—CH(OR1)-CH$_2$—O—R$^3$ in which R1, R2 and R3 denote, each independently of the others, $C_{11}H_{23}CO$, $C_{13}H_{27}CO$, $C_{15}H_{31}CO$ or $C_{17}H_{35}CO$. Mixtures of such triacyl glycerides can also be used.

Suitable thixotropic agent(s) which can be added to the composition of the invention are organic compounds e.g. waxes according to the definition in Ullmanns Enzyklopädie der technischen Chemie, 4. Auflage, Verlag Chemie, Weinheim, Band 24, page 3 or triglycerides as described in U.S. Pat. No. 6,127,449. In general all organic non-water based thixotropic agents are suitable. That means that suitable thixotropic agents can alter the rheology especially of non-water based formulation.

According to one embodiment of the invention, the composition can comprise the individual components in the following amounts:

Component (A): from about 5 wt.-% to about 97 wt.-% from about 12 wt.-% to about 90 wt.-% from about 45 wt.-% to about 60 wt.-%.

Component (B): from about 0.0001 wt.-% to about 35 wt.-% or from about 0.0005 wt.-% to about 20 wt.-% with respect to the whole composition.

Component (C): from about 0.1 wt.-% to about 7.5 wt.-% or from about 0.2 wt.-% to about 5 wt.-% with respect to the whole composition.

Component (D1): from about 0 wt.-% to about 7 wt.-% or from about 0.1 wt.-% to about 6 wt.-% or from about 0.5 wt.-% to about 5 wt.-% with respect to the whole composition.

Component (D2): from about 0 wt.-% to about 20 wt.-% or from about 0.01 wt.-% to about 15 wt.-% or from about 0.1 wt.-% to about 10 wt.-% with respect to the whole composition.

Component (E): from about 0 wt.-% to about 80 wt.-% or from about 0.2 wt.-% to about 75 wt.-% or from about 0.5 wt.-% to about 70 wt.-% with respect to the whole composition.

Component (F): from about 0 wt.-% to about 50 wt.-% or from about 0.005 wt.-% to about 40 wt.-% or from about 0.01 wt.-% to about 35 wt.-% with respect to the whole composition.

The dental composition according to the invention is typically provided in separate parts and comprises at least a curable base paste and a catalyst or initiator paste comprising a catalyst or initiator suitable for curing at least part of the material of the base paste.

Accordingly, the components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base paste and a catalyst paste separated from each other before use, wherein the base paste comprises component (A) and the catalyst paste comprises component (B) and wherein components (C), (D1), (D2), (E) and (F) is/are present either in the base paste or the catalyst paste or in the base paste and the catalyst paste.

The volume ratios of catalyst paste and base paste can range from about 10:1 to about 1:10. Particularly preferred volume ratios of base paste to catalyst paste are about 1:1 and about 5:1 (5 parts of base paste to 1 part of catalyst paste).

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. No. 5,924,600, U.S. Pat. No. 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as are described e.g. in U.S. Pat. No. 5,249,862, U.S. Pat. No. 5,286,105 and U.S. Pat. No. 5,332,122. The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2 or Pentamix™ 3.

In practice, the impression material can be syringed through a static or mechanical mixing device into an impression tray or onto the patient's teeth or tissue and placed in the patient's mouth. After the impression material is set, the tray is removed from the patient's mouth and, in instances where the dental practitioner prepares the positive model, it may be preferable to pour the positive model material immediately after removal of the impression from the patient's mouth.

If used in the dental field, the composition can be applied using e.g. the following steps:
providing the composition,
applying the composition to a surface,
letting the composition set.

The surface can be the surface of soft or hard oral tissue, the surface of an impression material, preferably of a cured impression material, the surface of a crown or the surface of a model of a tooth stump.

The invention also relates to a method of producing a curable composition comprising the step of combining an F-containing compound with a hardenable composition comprising components (A) and (B), wherein components (A), (B) and (C) are as described in the text of the present invention herein.

Typically, after combining of the F-containing compound with the individual components of the hardenable matrix, the components are mixed. The F-containing compound can be added to the other components of the composition from the very beginning of the production process or during or at the end of the production process.

The F-containing compound can also be applied as a premixture with component (A) and/or component (D1) and/or component (D2), if present.

The mixing step is typically done with a kneader but can also be accomplished by other means like a dissolver.

Some time after or during the mixing process, a de-gassing step is conducted. E.g., while the mixture is kneaded reduced pressure is applied helping to remove gaseous residues or gas from the mixture, gas which has been kneaded into the mixture during a kneading step.

If the F-containing compound of the present invention is used (e.g. compared to the ethoxylated nonionic fluorosurfactant Zonyl™ FSO-100 (DuPont), which is also described in WO 2007/080071), either the negative pressure applied to the mixture can be reduced even further before the mixture starts foaming or expanding, or the de-gassing step can be accomplished within a shorter period of time at a given negative pressure value.

In summary, using the F-containing compound of the present invention not only helps improving the hydrophilicity of the polyether group containing composition but also helps improving the manufacturing process.

The dental material or composition can be used as impression material or for the production of (temporary or long term) crown and/or bridges. In the latter case, the composition is used as a mould to be filled with the (temporary or long term) crown and/or bridge material, which is typically based on polymerizable (meth)acrylates or similar chemical reactants.

Another aspect of the invention, relates to a method of using the F-containing compound as a de-gassing agent and/or for improving the hydrophilicity of a hardenable composition, typically based on a dental composition as described above and optionally comprising one or more additional surfactant(s) as described above. The method typically includes the step of adding to or combining the F-containing compound with the other components for forming a hardenable matrix.

The curable composition is especially useful for producing dental materials like precision impression materials, bite registration materials, duplicating materials, modelling materials, situation impression materials.

In this respect, the composition can be used e.g. for making impressions of soft and hard dental tissue. This can be achieved simply, e.g. filling the material into a dental tray and putting the tray into the mouth of a patient.

If used in the dental field, curing is preferably carried out at a temperature below about 50° C. and preferably below about 40° C., and more preferably below about 30° C. A typical time for cure of curable compositions of the invention used for dental impressioning is within about 20 min, or preferably within about 10 min, after mixing the components of the composition. For dental duplicating applications or dental modelling applications that take place in the professional dental laboratory, cure times of up to 45 min is generally acceptable. In other applications (e.g., sealing, moulding, coating, adhesively fixing), other cure times may be typical and higher cure temperatures may be acceptable. Nevertheless, setting times in the range of about 30 min or about 1 hour can still be useful.

The material is generally regarded as cured, if the cured material fulfils the requirements for its use. For example, a dental precision impression material typically fulfils the requirements for its use when it fulfils the requirements of ISO 4823:2000 (such as compatibility with gypsum, strain in compression, recovery from deformation, detail reproduction, linear dimensional change).

Especially in the dental field two further parameters might be of some importance: working time and oral setting time.

The total working time at room temperature (23° C.) measured according to DIN EN ISO 4823:2000 for Impregum™ Garant L DuoSoft and Permadyne™ Garant L 2:1 (3M ESPE AG), both Type 3 regular setting polyether precision impression materials, is 3 min 40 s±15 s and 4 min±15 s, respectively. (According to DIN EN ISO 4823:2000 impression materials can be classified as Type 0 (kneadable), Type 1 (high viscosity), Type 2 (medium viscosity), and Type 3 (low viscosity).)

The oral setting time is given by the manufacturer in the instructions for use. According to DIN EN ISO 4823:2000 the elastomeric property recovery from deformation of the vulcanized material have to reach values of ≥96.5% within the recommended oral setting time. In addition according to DIN EN ISO 4823:2000 the elastomeric property strain in compression of the vulcanized material has to come up to a value within the range of 0.8 to 20.0% for Type 0 and Type 1 materials and in the range of 2.0 to 20.0% for Type 2 and Type 3 materials, respectively within the recommended oral setting time.

If the composition is to be used as dental impression material, appropriate working times are in a range of about 20 s to about 7 min or about 30 s to about 6 min at room temperature (23° C.). For impression materials oral setting times should be as short as possible. Suitable oral setting times are ≤about 6 min or ≤about 5 min.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, all molecular weights are weight average molecular weight and all measurements were done at ambient conditions (23° C.).

EXAMPLES

Measurement Methods

Shore A Hardness

The Shore A hardness of the compositions 6 min after mixing of the base and catalyst paste was determined according to DIN 53 505.

Determination of Setting Time

The setting time of the compositions was determined by measuring the viscosity of the mixed base and catalyst paste in dependence on the time at 23° C. and 50% humidity by using a MRC 301 rheometer (plate/plate measurement system) from Anton Paar. The setting time "te" as well as the working time "ta" were determined with the software supplied with the instrument.

Method of Production

The following components were used and mixed as outlined below (Table 1):

TABLE 1

| Component | Description | Availability |
|---|---|---|
| Zonyl™ FSO-100 | ethoxylated perfluoroalcanol | Aldrich or DuPont |
| HFPO-Amidol (z = 0-20, Mn = 1200-1300) | $CF_3$—$(CF_2)_2$—(O—$CF(CF_3)$—$CF_2)_z$—O—$CF(CF_3)$—$CONHCH_2CH_2OH$ | obtainable according to the description given in WO2004/060964 A1 |
| Silwet™ L-77 | | Momentive Performance Chemicals |
| Pluronic™ RPE 1740 | | BASF AG, Ludwigshafen |
| Impregum™ Soft Quick Step Tray (IST) | | 3M ESPE AG; Germany |
| Impregum™ Penta™ Soft (IPS) | | 3M ESPE AG; Germany |
| P2 Polyether Light | | Heraeus Kulzer, Germany |

General Description—Preparation of the Composition

According to Table 2, X wt.-% of the F-containing compound and optionally Y wt.-% of Silwet™ L-77 and Z wt.-% of Pluronic™ RPE 1740 were added to the base paste of Impregum™ Soft Quick Step Tray (IST, 3M ESPE), Impregum™ Penta™ Soft (IPS, 3M ESPE) or P2 Polyether Light (P2, Heraeus) kneaded two times for about 10 min and additional 10 min under vacuum (10 mbar). For the de-gassing experiments pastes without additional evacuation have been used.

For the IST system, base paste and catalyst paste have been mixed in a volume ratio of 2:1 (corresponding to a weight ration of about 1 part base paste and about 0.58 part catalyst paste) by hand using a spatula. As catalyst paste, the respective untreated catalyst paste [Impregum™ Soft Quick Step Tray (3M ESPE)] was used. Shore A hardness 6 min after mixing of base and catalyst paste and the setting time parameter "ta" and "te" were determined. The obtained values are summarized in Table 2.

The IPS base pastes were filled in foil bags which are compatible with the 3M ESPE Pentamix™ system. The foil bags were closed, a commercially available standard cap was attached and the system was inserted in a Pentamix cartridge. As catalyst paste, the respective commercially available (untreated) catalyst paste [Impregum™ Penta Soft (3M ESPE)] was used. The pastes were extruded and mixed using a Pentamix™2 (3M ESPE) mixing device (volume ratio base:catalyst=5:1) equipped with a dynamic mixing tip (3M ESPE).

TABLE 2

(amount of F-containing compound added)

| Wt.-% in base paste | | HFPO-Amidol | Zonyl FSO-100 | Silwet L-77 | Pluronic RPE 1740 |
|---|---|---|---|---|---|
| Example 1 | IST | 2.37 | — | — | — |
| Example 2 | IST | 2.37 | — | 2.37 | 2.37 |
| Comp. Example 1 | IST | — | — | — | — |
| Comp. Example 2 | IST | — | 2.37 | — | — |
| Comp. Example 3 | IST | — | 2.37 | 2.37 | 2.37 |
| Example 3 | IPS | 1.86 | — | — | — |
| Example 4 | IPS | 1.86 | — | 1.86 | 1.86 |
| Comp. Example 4 | IPS | — | — | — | — |
| Comp. Example 5 | IPS | — | 1.86 | — | — |
| Comp. Example 6 | IPS | — | 1.86 | 1.86 | 1.86 |
| Example 5 | P2 | 2.37 | — | — | — |
| Comp. Example 7 | P2 | — | — | — | — |
| Comp. Example 8 | P2 | — | 2.37 | — | — |

De-Gassing Experiments:

10 g of the non-evacuated base pastes according to Table 2 were placed uniformly flat on the bottom of a 250 ml beaker (Inner diameter: 6.5 cm) without contaminating the side walls of the beaker. The filled beaker was placed in a vacuum exsiccator and evacuated for 10 min below 10 mbar. The height of the foam is measured in the evacuated state with a ruler at the outside of the vacuum exsiccator. After ventilation, the height is measured again with a ruler as the height of the contamination on the wall of the beaker. The results for the different pastes are summarized in Table 3.

TABLE 3

| | | Height in mm (evacuated) | Height in mm (ventilated) |
|---|---|---|---|
| Example 1 | IST | 10 | 10 |
| Example 2 | IST | 10 | 10 |
| C.E.1 | IST | 30 | 20 |
| C.E.2 | IST | 50 | 35 |
| C.E.3 | IST | 50 | 30 |
| Example 3 | IPS | 10 | 10 |
| Example 4 | IPS | 10 | 10 |
| C.E.4 | IPS | 40 | 30 |
| C.E.5 | IPS | 50 | 30 |
| C.E.6 | IPS | 50 | 35 |
| Example 5 | P2 | 5 | 5 |
| C.E.7 | P2 | 20 | 10 |
| C.E.8 | P2 | 30 | 25 |

Setting Properties

The Shore hardness 6 min after mixing of base and catalyst paste and the setting time parameters "ta" and "te" were determined. The obtained values are summarized in Table 4. As can be seen for example 3 and 4 in comparison to C.E. 4, the addition of the fluorinated additive according to the invention leads to acceleration of te (setting time) whereas the working time is not affected. As can be seen from C.E. 5 and 6, such effects are not observed for systems comprising fluorinated surfactants according WO 2007/080071. Also a significant lower Shore hardness 6 min after mixing of base and catalyst paste indicate a retardation of the setting process in the presence of fluorinated surfactants, whereas for the inventive fluorinated additive no effect is observed. Thus, for the examples according to the invention an improved snap-set (te-ta) is observed.

TABLE 4

(Shore A hardness and setting time "ta" and "te")

| | Shore A hardness (6 min) | "ta" [min] | "te" [min] | te-ta |
|---|---|---|---|---|
| Example 3 | 22 | 2.09 | 3.90 | 1.81 |
| Example 4 | 24 | 2.19 | 4.01 | 1.71 |
| C.E. 4 | 24 | 2.15 | 4.52 | 2.02 |
| C.E. 5 | 20 | 2.31 | 4.83 | 2.52 |
| C.E. 6 | 19 | 2.37 | 4.71 | 2.34 |

The invention claimed is:

1. A curable dental composition comprising
a curable polyether group containing polymer as component (A), component (A) being a compound comprising polyalkylene oxide moieties,
an initiator capable of initiating a curing reaction of component (A) as component (B),
an F-containing compound as component (C),
wherein the F-containing compound is selected from the group of
Rf—(O)$_t$—CHF—(CF$_2$)$_x$-T, with t=0 or 1, x=0 or 1 and Rf being a linear or branched per- or partly fluorinated alkyl chain, wherein the per- or partly fluorinated alkyl chain can be interrupted by O atoms, with the proviso that when t is 0, Rf is a linear or branched per- or partly fluorinated alkyl chain interrupted by at least one oxygen atom,
Rf—(OCF$_2$)$_m$—O—CF$_2$-T, with m=1 to about 6 and Rf being a linear or branched per- or partly fluorinated alkyl chain, wherein the per- or partly fluorinated alkyl chain can be interrupted by O atoms,
CF$_3$—(CF$_2$)$_2$—(OCF(CF$_3$)—CF$_2$)$_z$—O-L-T, with z=0, 1, 2, 3, 4, 5, 6, 7 or 8 and L having a structure selected from —CF(CF$_3$)—, —CF$_2$— and —CF$_2$CF$_2$—, Rf—(O—CF$_2$CF$_2$)$_n$—O—CF$_2$-T, with n=1, 2, 3, 4 or 5 and Rf being a linear or branched per- or partly fluorinated alkyl chain, wherein the per- or partly fluorinated alkyl chain can be interrupted by O atoms, wherein T is selected from —COOR, —CONR$^b$R$^c$— CH$_2$OH, —CF$_2$OR, —CHFOH, —CHFOR, —CH$_2$OR or —F with R being a linear or branched alkyl (C1 to C9), aryl chain (C1 to C9) or alkylaryl (C1 to C9) each of which may optionally be substituted with one or more substituents selected from the group consisting of hydroxyl, amino group, halogen atom, an SiH group and a group capable of reacting with SiH, R$^b$ and R$^c$ independently representing H or having a meaning as given for R.

2. The dental composition of claim 1, wherein the F-containing compound is selected from Rf—O—CHF-T, with Rf being a linear or branched per- or partly fluorinated alkyl chain (C1 to C6), which can be interrupted by oxygen atoms, Rf—O—CHF—CF$_2$-T, with Rf being a linear or branched per- or partly fluorinated alkyl chain (C1 to C6), which can be interrupted by oxygen atoms, Rf—(O—CF$_2$)$_u$—O—CF$_2$-T, with Rf being a linear or branched per- or partly fluorinated alkyl chain (C1 to C6), which can be interrupted by oxygen atoms, and u=1, 2, 3, 4, 5 or 6, Rf—(O—CF$_2$—CF$_2$)$_k$—O—CF$_2$-T, with Rf being a linear or branched per- or partly fluorinated alkyl chain (C1 to C6), which can be interrupted by oxygen atoms, and k =1, 2, 3, 4 or 5, CF$_3$—(CF$_2$)$_2$—(OCF(CF$_3$)—CF$_2$)$_z$—O—CF(CF$_3$)-T, with z=0, 1, 2, 3, 4, 5, 6, 7 or 8, and mixtures thereof, T having the meaning as defined in claim 1.

3. The dental composition of claim 1, wherein the F-containing compound is selected from CF$_3$—(O—CF$_2$)$_3$—O—CF$_2$-T
CF$_3$—(O—CF$_2$)$_5$—O—CF$_2$-T
C$_2$F$_5$—(O—CF$_2$—CF$_2$)$_1$—O—CF$_2$-T
C$_3$F$_7$—(O—CF$_2$—CF$_2$)$_1$—O—CF$_2$-T
C$_4$F$_9$—(O—CF$_2$—CF$_2$)$_1$—O—CF$_2$-T
C$_2$F$_5$—(O—CF$_2$—CF$_2$)$_2$—O—CF$_2$-T
CF$_3$—(O—CF$_2$—CF$_2$)$_2$—O—CF$_2$-T
C$_3$F$_7$—(O—CF$_2$—CF$_2$)$_2$—O—CF$_2$-T
C$_4$F$_9$—(O—CF$_2$—CF$_2$)$_2$—O—CF$_2$-T
CF$_3$—(CF$_2$)$_2$—(O—CF(CF$_3$)—CF$_2$)$_2$—O—CF(CF$_3$)-T
CF$_3$—(CF$_2$)$_2$—(O—CF(CF$_3$)—CF$_2$)$_3$—O—CF(CF$_3$)-T
CF$_3$—(CF$_2$)$_2$—(O—CF(CF$_3$)—CF$_2$)$_4$—O—CF(CF$_3$)-T
CF$_3$—(CF$_2$)$_2$—(O—CF(CF$_3$)—CF$_2$)$_5$—O—CF(CF$_3$)-T
CF$_3$—(CF$_2$)$_2$—(O—CF(CF$_3$)—CF$_2$)$_6$—O—CF(CF$_3$)-T
and mixtures thereof, T having the meaning as defined in claim 1.

4. The dental composition of claim 1 further comprising at least one of the following components:
a Si-containing surfactant as component (D1),
a hydrocarbon surfactant as component (D2),
a filler as component (E),
additives as component (F) selected from retarder(s), rheology modifier(s), inhibitor(s), pigment(s), plasticizer(s), dye(s), pigment(s), odorous substance(s), flavouring(s), stabilizer(s), alone, in admixture or combination.

5. The dental composition of claim 4, wherein the components are present in the following amounts:
Component (A): from about 5 wt.-% to about 97 wt.-%,
Component (B): from about 0.1 wt.-% to about 35 wt.-%,
Component (C): from about 0.001 wt.-% to about 7.5 wt.-%,
Component (D1): from 0 wt.-% to about 7 wt.-%,
Component (D2): from 0 wt.-% to about 20 wt.-%,
Component (E): from 0 wt.-% to about 80 wt.-%,
Component (F): from 0 wt.-% to about 50 wt.-%,
wt.-% with respect to the weight of the whole composition.

6. The dental composition of claim 5, wherein component (D1) is selected from

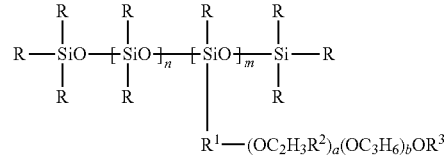

where each R is independently a monovalent hydrocarbyl radical with 1 to 22 C-atoms, R$^1$ is a divalent hydrocarbylene radical 1 to 26 C-atoms, each R$^2$ is independently hydrogen or a lower hydroxyalkyl radical, R$^3$ is hydrogen or a monovalent hydrocarbyl radical with 1 to 22 C-atoms, n and b are independently greater than or equal to 0, and m and a are independently greater than or equal to 1, or Q-P—(OC$_n$H$_{2n}$)$_x$—OZ, in which Q stands for R$_3$Si— or R$_3$Si—(R'—SiR$_2$)$_a$—R'—SiR"$_2$— where R in the molecule can be the same or different and can be an aliphatic C1-C18, a cycloaliphatic C6-C12 or an aromatic C6-C12 hydrocarbon radical, which can optionally be substituted by halogen atoms, R' is a C1-C14 alkylene group, R" is R in the case of a≠0 or is R or R$_3$SiR' in the case of a=0, and a=0-2; P represents a C2-C18 alkylene group or A-R'", where A represents a C2-C18 alkylene group and R'" a functional group selected from: —NHC(O)—, —NHC(O)—(CH$_2$)$_{n-1}$—, —NHC(O)C(O)—, —NHC(O)(CH$_2$)$_v$C(O)—, —OC (O)—, —OC(O)—(CH$_2$)$_{n-1}$—, —OC(O)C(O)—, —OC(O)(CH$_2$)$_v$C(O)—, —OCH$_2$CH(OH)CH$_2$OC(O) (CH$_2$)$_{n-1}$—, —OCH$_2$CH(OH)CH$_2$OC(O)(CH$_2$)$_v$C (O)— with v=1-12; Z is H or a C1-C4 alkyl radical or a C1-C4 acyl radical; x is a number from 1 to 200 and n a number from 1 to 6.

7. The dental composition of claim 5, wherein component (D1) is selected from

Q-P—(OC$_n$H$_{2n}$)$_x$—OT,

Q being R$_3$—Si— or R$_3$—Si—(R'—SiR$_2$)$_a$—R'—SiR"$_2$, where each R in the molecule can be the same or different and stands for an aliphatic C$_1$-C$_{18}$, a cycloaliphatic C$_6$-C$_{12}$ or an aromatic C$_6$-C$_{12}$ hydrocarbon radical, which can optionally be substituted by halogen atoms; R' is a C$_1$-C$_{14}$ alkylene group; R" is R in the case of a≠0 or is R or R$_3$SiR' in the case of a=0, and a =0 to 2; P stands for a C$_2$-C$_{18}$ alkylene group, or A-R'", where A represents a C$_2$-C$_{18}$ alkylene group and R'" a functional group from the following list: —NHC(O)—, —NHC (O)— (CH$_2$)$_{n-1}$—, —NHC(O)C(O)—, —NHC(O) (CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH$_2$)$_{n-1}$—, —OCH$_2$CH (OH)CH$_2$OC(O)(CH$_2$)$_v$C(O)— with v=1 to about 12; T is H or stands for a C1 to C4 alkyl radical or a C1 to C4 acyl radical; x stands for a number from 1 to about 200 and n stands for an average number from 1 to about 6.

8. The curable dental composition of claim 1, wherein component (A) is curable via a ring-opening polymerization reaction or via a hydrosilation reaction or via condensation reaction or via ring-opening metathesis reaction.

9. A kit of parts comprising a base paste and a catalyst paste separated from each other before use, wherein the base paste comprises component (A) and the catalyst paste comprises component (B) and wherein component (C), (D1), (D2), (E), and (F), if present, can be present either in the base paste or the catalyst paste or the base paste and the catalyst paste, wherein components (A) to (F) are as described in claim 4.

10. A curable dental composition comprising
a curable polyether group containing polymer as component (A), component (A) being a compound comprising polyalkylene oxide moieties,
an initiator capable of initiating a curing reaction of component (A) as component (B),
an F-containing compound as component (C),
wherein the F-containing compound is selected from the group of
Rf—O—CF$_2$-T, with Rf being a linear or branched per- or partly fluorinated alkyl chain (C1 to C6), which can be interrupted by oxygen atoms,
Rf—O—CF$_2$—CF$_2$-T, with Rf being a linear or branched per- or partly fluorinated alkyl chain (C1 to C6), which can be interrupted by oxygen atoms,
Rf—O—CF$_2$—CHF-T, with Rf being a linear or branched per- or partly fluorinated alkyl chain (C1 to C6), which can be interrupted by oxygen atoms,
Rf—O—CF$_2$—CHF—CF$_2$-T, with Rf being a linear or branched per- or partly fluorinated alkyl chain (C1 to C6), which can be interrupted by oxygen atoms,
Rf—(O—CF$_2$—CF$_2$—CF$_2$)$_n$—O—CF$_2$—CF$_2$-T, with n=1 to 25 and Rf being a linear or branched per- or partly fluorinated alkyl chain (C1 to C6), wherein the per- or partly fluorinated alkyl chain can be interrupted by O atoms,
T-CF$_2$—O—(CF$_2$—CF$_2$—O)$_p$—(CF$_2$—O)q-CF$_2$-T, with p/q=0.5 to 3.0; and an molecular weight in the range of about 500 to about 4000 g/mol,
T-CF$_2$—(O—CF(CF$_3$)—CF$_2$)$_n$—(O—CF$_2$)$_m$—O—CF$_2$-T, with n/m=20-40 and a molecular weight in the range of about 650 to about 3200 g/mol,
CF$_3$—(CF$_2$)$_2$—(OCF(CF$_3$)—CF$_2$)$_z$—O—CF(CF$_3$)-T, with z=0, 1, 2, 3, 4, 5, 6, 7 or 8,
CF$_3$—CHF—O—(CF$_2$)$_o$-T, with o=1, 2, 3, 4, 5 or 6,
CF$_3$—CF$_2$—O—(CF$_2$)$_o$-T, with o=1, 2, 3, 4, 5 or 6,
and mixtures thereof,
wherein T is selected from —COOR, —CONR$^b$R$^c$— CH$_2$OH, —CF$_2$OR, —CHFOH, —CHFOR, —CH$_2$OR or —F.

11. The dental composition of claim 10 further comprising at least one of the following components:
an Si-containing surfactant as component (D1),
an hydrocarbon surfactant as component (D2),
filler as component (E),
additives as component (F) selected from retarder(s), rheology modifier(s), inhibitor(s), pigment(s), plasticizer(s), dye(s), pigment(s), odorous substance(s), flavouring(s), stabilizer(s), alone, in admixture or combination.

12. The dental composition of claim 11, wherein the components are present in the following amounts:
Component (A): from about 5 wt.-% to about 97 wt.-%,
Component (B): from about 0.1 wt.-% to about 35 wt.-%,
Component (C): from about 0.001 wt.-% to about 7.5 wt.-%,
Component (D1): from 0 wt.-% to about 7 wt.-%,
Component (D2): from 0 wt.-% to about 20 wt.-%,
Component (E): from 0 wt.-% to about 80 wt.-%,
Component (F): from 0 wt.-% to about 50 wt.-%,
wt.-% with respect to the weight of the whole composition.

13. The dental composition of claim 12, wherein component (D1) is selected from

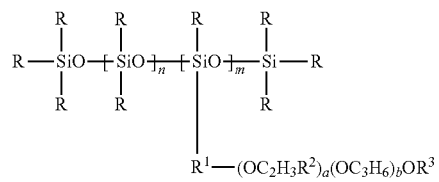

where each R is independently a monovalent hydrocarbyl radical with 1 to 22 C-atoms, R$^1$ is a divalent hydrocarbylene radical 1 to 26 C-atoms, each R$^2$ is independently hydrogen or a lower hydroxyalkyl radical, R$^3$ is hydrogen or a monovalent hydrocarbyl radical with 1 to 22 C-atoms, n and b are independently greater than or equal to 0, and m and a are independently greater than or equal to 1,
or
Q-P—(OC$_n$H$_{2n}$)$_x$—OZ, in which Q stands for R$_3$Si— or R$_3$Si—(R'—SiR$_2$)$_a$R'—SiR''$_2$—
where R in the molecule can be the same or different and can be an aliphatic C1-C18, a cycloaliphatic C6-C12 or an aromatic C6-C12 hydrocarbon radical, which can optionally be substituted by halogen atoms, R' is a C1-C14 alkylene group, R'' is R in the case of a≠0 or is R or R$_3$SiR' in the case of a=0, and a=0-2; P represents a C2-C18 alkylene group or A-R''', where A represents a C2-C18 alkylene group and R''' a functional group selected from: —NHC(O)—, —NHC(O)—(CH$_2$)$_{n-1}$—, —NHC(O)C(O)—, —NHC(O)(CH$_2$)$_v$C(O)—, —OC (O)—, —OC(O)—(CH$_2$)$_{n-1}$—, —OC(O)C(O)—, —OC(O)(CH$_2$)$_v$C(O)—, —OCH$_2$CH(OH)CH$_2$OC(O) (CH$_2$)$_{n-1}$—, —OCH$_2$CH(OH)CH$_2$OC(O)(CH$_2$)$_v$C (O)— with v=1-12; Z is H or a C1-C4 alkyl radical or a C1-C4 acyl radical; x is a number from 1 to 200 and n a number from 1 to 6.

14. The dental composition of claim 12, wherein component (D1) is selected from
Q-P—(OC$_n$H$_{2n}$)$_x$—OT,
Q being R$_3$—Si— or R$_3$—Si—(R'—SiR$_2$)$_a$—R'—SiR''$_2$,
where each R in the molecule can be the same or different and stands for an aliphatic C$_1$-C$_{18}$, a cycloaliphatic C$_6$-C$_{12}$ or an aromatic C$_6$-C$_{12}$ hydrocarbon radical, which can optionally be substituted by halogen atoms; R' is a C$_1$-C$_{14}$ alkylene group; R'' is R in the case of a≠0 or is R or R$_3$SiR' in the case of a=0, and a =0 to 2; P stands for a C$_2$-C$_{18}$ alkylene group, or A-R''', where A represents a C$_2$-C$_{18}$ alkylene group and R''' a functional group from the following list: —NHC(O)—, —NHC (O)— (CH$_2$)$_{n-1}$—, —NHC(O)C(O)—, —NHC(O) (CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH$_2$)$_{n-1}$—, —OCH$_2$CH (OH)CH$_2$OC(O)(CH$_2$)$_v$C(O)— with v=1 to about 12; T is H or stands for a C1 to C4 alkyl radical or a C1 to C4 acyl radical; x stands for a number from 1 to about 200 and n stands for an average number from 1 to about 6.

15. The curable dental composition of claim 10, wherein component (A) is curable via a ring-opening polymerization reaction or via a hydrosilation reaction or via condensation reaction or via ring-opening metathesis reaction.

16. A kit of parts comprising a base paste and a catalyst paste separated from each other before use, wherein the base paste comprises component (A) and the catalyst paste comprises component (B) and wherein component (C), (D1), (D2), (E), and (F), if present, can be present either in the base paste or the catalyst paste or the base paste and the catalyst paste, wherein components (A) to (F) are as described in claim 11.

17. A curable dental composition comprising
a curable polyether group containing polymer as component (A), component (A) being a compound comprising polyalkylene oxide moieties,
an initiator capable of initiating a curing reaction of component (A) as component (B),
an F-containing compound as component (C),
wherein the F-containing compound is selected from the group of
$CF_3$—O—$CF_2$—O—$CF_2$—$CF_2$—O—CHF-T
$CF_3$—(O—$CF_2$)$_2$—O—$CF_2$—$CF_2$—O—CHF-T
$CF_3$—(O—$CF_2$)$_3$—O—$CF_2$—$CF_2$—O—CHF-T
$CF_3$—O—$CF_2$—O—$CF_2$—$CF_2$—O—CHF—$CF_2$-T
$CF_3$—(O—$CF_2$)$_2$—O—$CF_2$—$CF_2$—O—CHF—$CF_2$-T
$CF_3$—(O—$CF_2$)$_3$—O—$CF_2$—$CF_2$—O—CHF—$CF_2$-T
$C_3F_7$—O—$CF_2$—CHF-T
$CF_3$—O—$CF_2$—O—$CF_2$—$CF_2$—O—$CF_2$—CHF-T
$CF_3$—(O—$CF_2$)$_2$—O—$CF_2$—$CF_2$—O—$CF_2$—CHF-T
$CF_3$—(O—$CF_2$)$_3$—O—$CF_2$—$CF_2$—O—$CF_2$—CHF-T
$C_3F_7$—O—$CF_2$—CHF—$CF_2$-T
$CF_3$—O—$CF_2$—$CF_2$—$CF_2$—O—$CF_2$—CHF—$CF_2$-T
$CF_3$—O—$CF_2$—O—$CF_2$—$CF_2$—O—$CF_2$—CHF—$CF_2$-T
$CF_3$—(O—$CF_2$)$_2$—O—$CF_2$—$CF_2$—O—$CF_2$—CHF—$CF_2$-T
$CF_3$—(O—$CF_2$)$_3$—O—$CF_2$—$CF_2$—O—$CF_2$—CHF—$CF_2$-T
$CF_3$—CFH—O—$(CF_2)_3$-T
$CF_3$—CFH—O—$(CF_2)_5$-T
$CF_3$—$CF_2$—O—$(CF_2)_3$-T
$CF_3$—$CF_2$—O—$(CF_2)_5$-T
Rf—(O—$CF_2$—$CF_2$—$CF_2$)$_n$—O—$CF_2$—$CF_2$-T, with n=1 to 25 and Rf being a linear or branched per- or partly fluorinated alkyl chain (C1 to C6), wherein the per- or partly fluorinated alkyl chain can be interrupted by O atoms,
T-$CF_2$—O—$(CF_2$—$CF_2$—O$)_p$—$(CF_2$—O$)_q$—$CF_2$-T, with p/q=0.5 to 3.0 and an molecular weight in the range of about 500 to about 4000 g/mol,
T-$CF_2$—(O—CF($CF_3$)—$CF_2$)$_n$—(O—$CF_2$)$_m$—O—$CF_2$-T, with n/m=about 20 to 40 and a molecular weight in the range of about 650 to about 3200 g/mol,
and mixtures thereof,
wherein T is selected from —COOR, —CONR$^b$R$^c$—CH$_2$OH, —CF$_2$OR, —CHFOH, —CHFOR, —CH$_2$OR or —F.

18. The dental composition of claim 17 further comprising at least one of the following components:
a Si-containing surfactant as component (D1),
a hydrocarbon surfactant as component (D2),
a filler as component (E),
additives as component (F) selected from retarder(s), rheology modifier(s), inhibitor(s), pigment(s), plastizer(s), dye(s), pigment(s), odorous substance(s), flavouring(s), stabilizer(s), alone, in admixture or combination.

19. The dental composition of claim 18, wherein the components are present in the following amounts:
Component (A): from about 5 wt.-% to about 97 wt.-%,
Component (B): from about 0.1 wt.-% to about 35 wt.-%,
Component (C): from about 0.001 wt.-% to about 7.5 wt.-%,
Component (D1): from 0 wt.-% to about 7 wt.-%,
Component (D2): from 0 wt.-% to about 20 wt.-%,
Component (E): from 0 wt.-% to about 80 wt.-%,
Component (F): from 0 wt.-% to about 50 wt.-%,
wt.-% with respect to the weight of the whole composition.

20. The dental composition of claim 19, wherein component (D1) is selected from

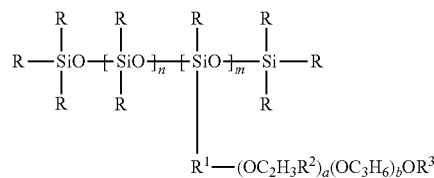

where each R is independently a monovalent hydrocarbyl radical with 1 to 22 C-atoms, R$^1$ is a divalent hydrocarbylene radical 1 to 26 C-atoms, each R$^2$ is independently hydrogen or a lower hydroxyalkyl radical, R$^3$ is hydrogen or a monovalent hydrocarbyl radical with 1 to 22 C-atoms, n and b are independently greater than or equal to 0, and m and a are independently greater than or equal to 1,
or
Q-P—$(OC_nH_{2n})_x$—OZ, in which Q stands for R$_3$Si— or R$_3$Si—(R'—SiR$_2$)$_a$—R'—SiR''$_2$—
where R in the molecule can be the same or different and can be an aliphatic C1-C18, a cycloaliphatic C6-C12 or an aromatic $C_6$-$C_{12}$ hydrocarbon radical, which can optionally be substituted by halogen atoms, R' is a C1-C14 alkylene group, R'' is R in the case of a≠0 or is R or R$_3$SiR' in the case of a=0, and a=0-2; P represents a C2-C18 alkylene group or A-R''', where A represents a C2-C18 alkylene group and R''' a functional group selected from: —NHC(O)—, —NHC(O)—(CH$_2$)$_{n-1}$—, —NHC(O)C(O)—, —NHC(O)(CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH$_2$)$_{n-1}$—, —OCH$_2$CH(OH)CH$_2$OC(O)(CH$_2$)$_v$C(O)— with v=1-12; Z is H or a C1-C4 alkyl radical or a C1-C4 acyl radical; x is a number from 1 to 200 and n a number from 1 to 6.

21. The dental composition of claim 19, wherein component (D1) is selected from
Q-P—$(OC_nH_{2n})_x$—OT,
Q being R$_3$—Si— or R$_3$—Si—(R'—SiR$_2$)$_a$—R'—SiR''$_2$,
where each R in the molecule can be the same or different and stands for an aliphatic $C_1$-$C_{18}$, a cycloaliphatic $C_6$-$C_{12}$ or an aromatic $C_6$-$C_{12}$ hydrocarbon radical, which can optionally be substituted by halogen atoms; R' is a $C_1$-$C_{14}$ alkylene group; R'' is R in the case of a≠0 or is R or R$_3$SiR' in the case of a=0, and a =0 to 2; P stands for a $C_2$-$C_{18}$ alkylene group, or A-R''', where A represents a $C_2$-$C_{18}$ alkylene group and R''' a functional group from the following list: —NHC(O)—, —NHC(O)— (CH$_2$)$_{n-1}$—, —NHC(O)C(O)—, —NHC(O)(CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH$_2$)$_{n-1}$—, —OCH$_2$CH(OH)CH$_2$OC(O)(CH$_2$)$_v$C(O)— with v=1 to about 12; T is H or stands for a C1 to C4 alkyl radical or a C1 to C4 acyl radical; x stands for a number from 1 to about 200 and n stands for an average number from 1 to about 6.

22. The curable dental composition of claim 17, wherein component (A) is curable via a ring-opening polymerization reaction or via a hydrosilation reaction or via condensation reaction or via ring-opening metathesis reaction.

23. A kit of parts comprising a base paste and a catalyst paste separated from each other before use, wherein the base paste comprises component (A) and the catalyst paste comprises component (B) and wherein component (C), (D1), (D2), (E), and (F), if present, can be present either in the base paste or the catalyst paste or the base paste and the catalyst paste, wherein components (A) to (F) are as described in claim 18.

* * * * *

UNITED STATES PATENT AND TRADEMARK OFFICE
CERTIFICATE OF CORRECTION

PATENT NO. : 8,962,708 B2
APPLICATION NO. : 13/322970
DATED : February 24, 2015
INVENTOR(S) : Andreas R. Maurer et al.

It is certified that error appears in the above-identified patent and that said Letters Patent is hereby corrected as shown below:

In the specification,

Column 1

Line 46, after "composition" delete "i.a.".

Column 2

Line 39, delete "mono-valent" and insert -- monovalent --, therefor.

Column 6

Line 66, delete "moities," and insert -- moieties, --, therefor.

Column 7

Lines 31-32, delete "Silwett" and insert -- Silwet --, therefor.

Column 9

Line 26, delete "prop" and insert -- Drop --, therefor.

Column 9

Line 61, delete "1-shaped" and insert -- l-shaped --, therefor.

Column 12

Line 26, delete "aziridene" and insert -- aziridine --, therefor.

Signed and Sealed this
Twenty-second Day of March, 2016

Michelle K. Lee
*Director of the United States Patent and Trademark Office*

Column 13

Line 50, delete "silic acid," and insert -- silicic acid, --, therefor.

Column 13

Line 51, delete "polysilic acid" and insert -- polysilicic acid --, therefor.

Column 13

Line 60 (approx.), delete "$R^{z}O-[Si(OR^{z})]_{n1}-Si(OR^{z})_{3}$" and insert -- $R^{z}O\text{-}[Si(OR^{z})_{2}]_{n1}\text{-}Si(OR^{z})_{3}$ --, therefor.

Column 17

Line 57, delete "tetrafluorooxetane" and insert -- tetrafluorooxetane. --, therefor.

Column 17

Line 61, delete "oxygen" and insert -- oxygen. --, therefor.

Column 19

Line 58, delete "perfluorated" and insert -- perfluorinated --, therefor.

Column 23

Line 63, delete "plastizer(s)," and insert -- plasticizer(s), --, therefor.

Column 24

Line 28, delete "acides" and insert -- acids --, therefor.

Column 24

Line 28, delete "solfonic" and insert -- sulfonic --, therefor.

Column 24

Line 29, delete "solfonic" and insert -- sulfonic --, therefor.

Column 29

Line 13, delete "ration" and insert -- ratio --, therefor.

CERTIFICATE OF CORRECTION (continued)
U.S. Pat. No. 8,962,708 B2

In the claims,

Column 31

Line 59, in Claim 4, delete "plastizer(s)," and insert -- plasticizer(s), --, therefor.

Column 32

Line 36, in Claim 6, delete "R''' a" and insert -- R''' is a --, therefor.

Column 32

Line 36, in Claim 6, delete "R''' a" and insert -- R''' is a --, therefor.

Column 32

Line 43, in Claim 6, delete "n a" and insert -- n is a --, therefor.

Column 33

Line 57, in Claim 11, delete "plastizer(s)," and insert -- plasticizer(s), --, therefor.

Column 34

Line 26, in Claim 13, delete "$R_3Si-(R'-SiR_2)_aR'-SiR''_2-$" and insert -- $R_3Si-(R'-SiR_2)_a-R'-SiR''_2-$ --, therefor.

Column 34

Line 34, in Claim 13, delete "R''' a" and insert -- R''' is a --, therefor.

Column 34

Line 41, in Claim 13, delete "n a" and insert -- n is a --, therefor.

Column 35

Line 61, in Claim 18, delete "plastizer(s)," and insert -- plasticizer(s), --, therefor.